United States Patent
Burt et al.

(10) Patent No.: US 9,644,359 B2
(45) Date of Patent: *May 9, 2017

(54) LAVATORY TREATMENT DEVICE

(71) Applicant: Reckitt Benckiser LLC, Parsippany, NJ (US)

(72) Inventors: Diane Joyce Burt, Montvale, NJ (US); Priscila Mira Luciano, Montvale, NJ (US)

(73) Assignee: RECKITT BENCKISER LLC, Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/413,880

(22) PCT Filed: Jul. 15, 2013

(86) PCT No.: PCT/GB2013/051887
§ 371 (c)(1),
(2) Date: Jan. 9, 2015

(87) PCT Pub. No.: WO2014/013236
PCT Pub. Date: Jan. 23, 2014

(65) Prior Publication Data
US 2015/0159358 A1    Jun. 11, 2015

Related U.S. Application Data

(60) Provisional application No. 61/672,029, filed on Jul. 16, 2012, provisional application No. 61/683,879, (Continued)

(51) Int. Cl.
*C11D 1/29* (2006.01)
*E03D 9/03* (2006.01)
(Continued)

(52) U.S. Cl.
CPC .............. *E03D 9/032* (2013.01); *A61L 9/048* (2013.01); *A61L 9/05* (2013.01); *C11D 1/58* (2013.01);
(Continued)

(58) Field of Classification Search
None
See application file for complete search history.

(56) References Cited

U.S. PATENT DOCUMENTS

2009/0215661 A1* 8/2009 Klinkhammer .......... C11D 3/18
510/192

FOREIGN PATENT DOCUMENTS

WO    2009105233 A1    8/2009
WO    2010001092 A1    1/2010

OTHER PUBLICATIONS

International Search Report for PCT/GB2013/051887 dated Oct. 8, 2013.
(Continued)

*Primary Examiner* — Necholus Ogden, Jr.
(74) *Attorney, Agent, or Firm* — Norris McLaughlin & Marcus PA

(57) ABSTRACT

Lavatory treatment devices comprise a lavatory treatment composition which includes:
 up to 50% wt. of an adhesion promoter constituent based on a fatty alcohol polyglycol ether as may be represented by the following structural formula (I):

$$R-O-[CH_2-CH_2-O-]_nH \qquad (I)$$

Figure 1:
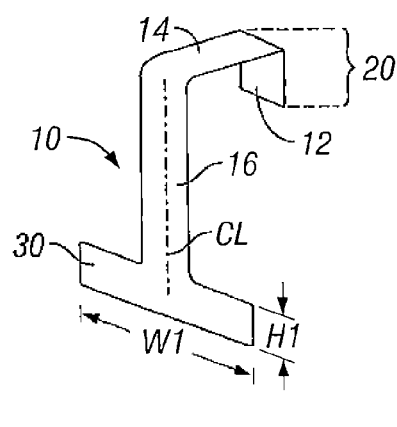

within which, R is an $C_{12}$-$C_{24}$ aliphatic mono- or polyalkene moiety, and n has a value of from 1 to 50;
 0.01-25% wt. of an organic solvent constituent, which is liquid at room temperature (20° C.);
 0.1-25% wt. of a detersive surfactant constituent;
(Continued)

optionally a co-adhesion promoter constituent, preferably based on one or more oxyalkylenated compounds;

further optionally one or more further optional constituents which may impart a further aesthetic or technical benefit to the said lavatory treatment compositions; and, to 100% wt. of water.

Preferably the lavatory treatment compositions of the lavatory treatment devices are ringing gels.

12 Claims, 15 Drawing Sheets

Related U.S. Application Data filed on Aug. 16, 2012, provisional application No. 61/724,758, filed on Nov. 9, 2012.

(51) Int. Cl.
| | |
|---|---|
| *A61L 9/04* | (2006.01) |
| *A61L 9/05* | (2006.01) |
| *C11D 3/43* | (2006.01) |
| *C11D 17/04* | (2006.01) |
| *E03D 9/00* | (2006.01) |
| *E03D 9/02* | (2006.01) |
| *C11D 1/835* | (2006.01) |
| *C11D 1/86* | (2006.01) |
| *C11D 17/00* | (2006.01) |
| *C11D 1/58* | (2006.01) |
| *C11D 3/20* | (2006.01) |
| *C11D 1/72* | (2006.01) |
| *C11D 1/62* | (2006.01) |

(52) U.S. Cl.
CPC .............. *C11D 1/835* (2013.01); *C11D 1/86* (2013.01); *C11D 3/2065* (2013.01); *C11D 3/2068* (2013.01); *C11D 3/43* (2013.01); *C11D 17/003* (2013.01); *C11D 17/0056* (2013.01); *C11D 17/044* (2013.01); *E03D 9/005* (2013.01); *E03D 9/022* (2013.01); *C11D 1/29* (2013.01); *C11D 1/62* (2013.01); *C11D 1/72* (2013.01); *E03D 2009/024* (2013.01); *E03D 2009/026* (2013.01)

(56) References Cited

OTHER PUBLICATIONS

Written Opinion of the International Searching Authority for PCT/GB2013/051887 dated Oct. 8, 2013.

\* cited by examiner

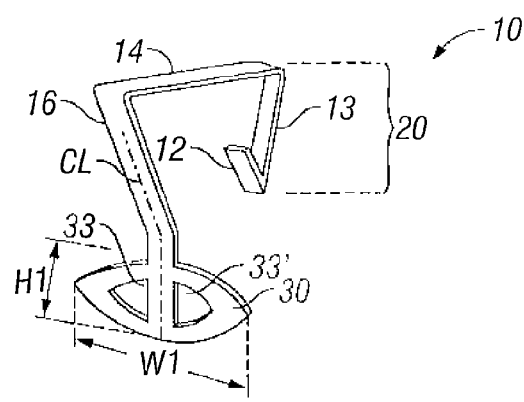
Fig. 5
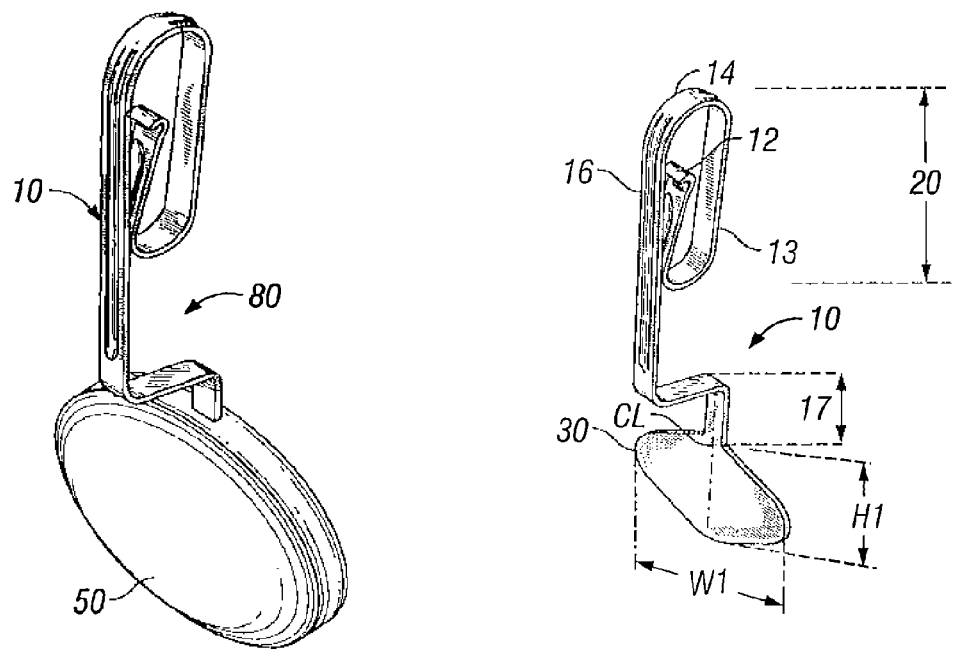
Fig. 6B
Fig. 6A

LAVATORY TREATMENT DEVICE

This is an application filed under 35 USC 371 of PCT/GB2013/051887, which in turn claims the priority benefits to the following further applications: U.S. Ser. No. 61/672,029 filed 16 Jul. 2012; US Serial No. 29/61/683879 filed 16 Aug. 2012; U.S. Ser. No. 61/724,758 filed 9 Nov. 2012.

The present invention relates to lavatory treatment devices which are adapted to be used in the treatment of a lavatory appliance, e.g., a toilet bowl.

Generally speaking, lavatory treatment compositions used to treat lavatory appliances, e.g., toilet bowls, bidets, urinals, etc. are notoriously old in the art, as since the advent of such sanitary appliances, there has been a continuing need in the art to provide effective ways to maintain these appliances in a satisfactory condition between uses. The art is replete with devices which are intended to be used as "in the bowl" (or ITB) or "in the cistern" (or ITC) in order to provide a coloring and/or cleaning and/or fragrancing and/or sanitizing effect to such sanitary devices, particularly toilet bowls.

One common approach known to the art is to provide a device which is at least partially immersed within the cistern or tank of a toilet, which may be either placed wholly within the interior of the toilet such as by placement at the bottom of a toilet tank so that the entire device is wholly immersed in water when the tank is full, or is at least partially immersed within the water present in a toilet tank, such as wherein such a device is suspended from a part of the toilet tank, such as a lip or rim of the tank. Such are generally referred to as ITC devices.

A further common approach known to the art is to provide a device which is suspended from the rim of the toilet bowl and which is placed at or near the interior sidewall of the toilet bowl. Such are generally referred to as ITB devices. Such a device is designed to typically dispense a treatment composition to the interior of a toilet when a gel or block compositions is contacted with flushing water, or alternately, dispensing a fragrancing composition to the toilet bowl which is intended to counteract or mask malodors. Typically such devices include a hanger portion which is used to suspend a cage portion from the rim of the toilet bowl, such that the cage portion is positioned within the path of flowing water which is dispensed with each flush operation of the toilet. The cage portion typically comprises a plurality of holes or apertures which permit for the flush water to both enter and to exit the cage portion of the device. Typically a solid block composition or a gel composition is present within the cage. The solid block composition and/or gel composition typically comprises one or more cleaning constituents, e.g., one or more surfactants which provide a good cleaning and/or foaming benefit. The cage acts then as a porous receptacle and support for said block composition or a gel composition as such permits for the impingement of water present within the lavatory appliance to come into contact with the block composition or a gel composition, which is thereby eluted into the water for form a lavatory treatment liquid. Such a cage may be used in an ITC application such that the block composition or a gel composition is suspended within the water present in the cistern of a toilet or other water supply tank. Such a cage may also be used in an ITB application wherein the block composition or a gel composition is suspended within or be placed within the interior of a lavatory appliance, e.g., a toilet bowl, bidet or urinal, wherein the block composition or gel composition comes into contact with the flush water when the lavatory appliance is used.

By way of non-limiting examples, certain lavatory treatment compositions which also exhibit an adhesive property include those disclosed in U.S. Pat. No. 6,667,286, EP 1978080 A1, as well as US 2009/0325839.

Notwithstanding the availability of various such devices, there remains a real and continuing need in the art for improved lavatory treatment devices, as well as improved lavatory treatment devices which include improved lavatory treatment compositions from which they may be dispensed to a lavatory appliance.

In a first aspect there is provided a lavatory treatment device which comprises a lavatory treatment composition which comprises (or, consists essentially of, or consists of):

up to 50% wt. of an adhesion promoter constituent based on a fatty alcohol polyglycol ether as may be represented by the following structural formula (I):

within which, R is an $C_{12}$-$C_{24}$ aliphatic mono- or polyalkene moiety, and n has a value of from 1 to 50;

0.01-25% wt. of an organic solvent constituent, which is liquid at room temperature (20° C.);

0.1-25% wt. of a detersive surfactant constituent;

optionally a co-adhesion promoter constituent, preferably based on one or more oxyalkylenated compounds;

further optionally one or more further optional constituents which may impart a further aesthetic or technical benefit to the said lavatory treatment compositions; and, to 100% wt. of water.

In preferred embodiments the foregoing lavatory treatment compositions also exhibit a degree of as adhesivity, as they are "self-adhesive" to ceramic surfaces or porcelain, which materials are commonly used in the manufacture of various lavatory appliances. This property may also be advantageous in retaining the lavatory treatment compositions within or upon the lavatory treatment device, of which it forms a part thereof.

In a further aspect of the invention, there is provided a lavatory treatment device which comprises a lavatory treatment composition as described above which comprises at least two different adhesion promoters, each based on a fatty alcohol polyglycol ether as may be represented by the following structural formula (I):

within which, R is an $C_{12}$-$C_{24}$ aliphatic mono- or polyalkene moiety, and n has a value of from 1 to 50.

In a further aspect of the invention, there is provided a lavatory treatment device which comprises a lavatory treatment composition as described above which comprises at least one cationic surfactant as the detersive surfactant constituent.

In a further aspect the present invention provides methods for the manufacture of the lavatory treatment device which comprises a lavatory treatment composition disclosed herein.

In a yet further aspect, the present invention provides a method for the use of the lavatory treatment devices described herein, in the treatment of lavatory appliances, and especially toilet bowls.

Further features and aspects of the present invention will become more apparent from a further reading of the present specification.

All aspects of the lavatory treatment device of the invention necessarily comprise a lavatory treatment composition as described herein.

A first essential constituent of the lavatory treatment composition is at least one adhesion promoter based on a fatty alcohol polyglycol ether, as may be represented by the following structural formula (I):

  (I)

within which:

R is an $C_{12}$-$C_{24}$ aliphatic mono- or poly-alkene moiety, and n has a value of from 1 to 50, but preferably n has a value of from 5 to 40, and most preferably has a value of from 25 to 35, inclusive.

Such a mono-alkene moieties includes only a single unsaturation between two adjacent carbon atoms, while a poly-alkene moiety includes at least two unsaturations between an appropriate number of carbon atoms in the R residue. Preferably R is a residue of a $C_{12}$-$C_{24}$ fatty alcohol having only one unsaturated bond between adjacent carbon atoms, viz., monounsaturation, although the residue of a $C_{12}$-$C_{24}$ fatty alcohol may also be polyunsaturated, having at least two unsaturated bonds between adjacent carbon atoms in the $C_{12}$-$C_{24}$ fatty alcohol residue. While R may have one or more branches, it is preferably linear. Mixtures or blends of two or more R residues, especially where such R residues are based on $C_{12}$-$C_{24}$ fatty alcohols may also be used.

In preferred embodiments the adhesion promoter based on a fatty alcohol glycol ether, conforms to the foregoing structural formula and comprises one or more unsaturations within the midsection of the R moiety, which is preferably a $C_{12}$-$C_{24}$ fatty alcohol, e.g, wherein the location of the at least one unsaturation (preferably a single unsaturation is present) is within the interior portion of the carbon molecules as measured from the midpoint of the $C_{12}$-$C_{24}$ aliphatic mono- or poly-alkene moiety and extending outwardly therefrom from both sides from the central carbon(s) which is/are equidistant from the two most distal carbon atoms of the longest carbon chain in the $C_{12}$-$C_{24}$ aliphatic mono- or poly-alkene moiety. Thus for example, if the R is a linear $C_{14}$ fatty alcohol, which is an even numbered fatty alcohol, then the central carbon(s) are the $C_7$ and $C_8$ carbons which are also at the midpoint as measured from the distal, $C_1$ and $C_{14}$ carbons of this fatty alcohol. Where, for example R is an odd numbered fatty alcohol, e.g. where R is a $C_{15}$ fatty alcohol, then the central carbon is the $C_8$ alcohol which is at the midpoint, as being equidistant from both the $C_1$ and $C_{15}$ carbons of the fatty alcohol. The midpoint carbon(s) may also be identified by the following equation:

$N/2$=midpoint carbon(s)

wherein:

N is the number of carbon atoms in the longest carbon chain in the $C_{12}$-$C_{24}$ aliphatic mono- or poly-alkene moiety, corresponding to R in the foregoing structural formula. Wherein "N" is an even number then the foregoing equation will yield a value with no decimal remainder (e.g., for a $C_{14}$ aliphatic mono- or poly-alkene moiety, N=14, and thus N/2=7), then the midpoint carbons are the N/2 carbon, and the adjacent (N/2)+1 carbon. Such corresponds to the $7^{th}$ and $8^{th}$ carbons in the $C_{14}$ aliphatic mono- or poly-alkene moiety. Wherein "N" is an odd number then the foregoing equation will yield a value with a "0.5" decimal remainder, (e.g., for a $C_{15}$ aliphatic mono- or poly-alkene moiety, N=15, and thus N/2=7.5), then the midpoint carbons is (N/2)+0.5 carbon. Such corresponds to the $8^{th}$ carbon atom in the $C_{15}$ aliphatic mono- or poly-alkene moiety.

Preferably the one or more unsaturations present with the $C_{12}$-$C_{24}$ aliphatic mono- or poly-alkane moiety are between adjacent carbon atoms which are between the (N–N+2) carbon atoms and the (N–2) carbon atoms, and in order of increasing preference are: between the (N–N+4) carbon atoms and the (N–4) carbon atoms, and between the (N–N+5) carbon atoms and the (N–5) carbon atoms of the $C_{12}$-$C_{24}$ aliphatic mono- or poly-alkene moiety.

Preferably the one or more unsaturations present with the $C_{12}$-$C_{24}$ aliphatic mono- or poly-alkene moiety are between adjacent carbons which are within four carbons adjacent to one or both of the midpoint carbon(s), preferably are within three carbons adjacent to the one or both of the midpoint carbon(s), and especially preferably is/are between adjacent carbon atoms at least one of which is the midpoint carbon(s) in the longest carbon chain in the $C_{12}$-$C_{24}$ aliphatic mono- or poly-alkene moiety.

Particularly preferred fatty alcohol glycol ethers of the foregoing structural formula (I) include those which have two or less unsaturations in the R residue, and particularly preferred are those which have a single unsaturation in the R residue.

In certain preferred embodiments the R residue of the fatty alcohol polyglycol ether of the foregoing structural formula (I) is derived from a monounsaturated fatty alcohol which may be represented by the following formula (II):

$CH_3(CH_2)_x CH=CH(CH_2)_y$—$CH_2OH$  (II)

in which each of x and y are integers which have a value in the range of 6-32, preferably in the range of 8-18, and further preferably the value of x:y are within the respective ratios of from 0.5:1-1:0.5 preferably 0.75:1-1:0.75, and especially preferably about 1:1. Such is a monounsaturated alcohol. Preferably the fatty alcohol of the R residue is based on oleyl alcohol, preferably a monounsaturated oleyl alcohol.

Preferred fatty alcohol glycol ethers of the foregoing structural formula (I) include those which are presently commercially available in the Genapol® "O" series of nonionic surfactants which include:

| Genapol O 020 | oleyl alcohol polyglycol ether (2 EO) 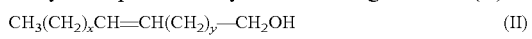 |
|---|---|
| Genapol O 050 | oleyl alcohol polyglycol ether (5 EO) R—O—[CH₂CH₂O]₅H |
| Genapol O 080 | oleyl alcohol polyglycol ether (8 EO) R—O—[CH₂CH₂O]₈H |
| Genapol O 100 | oleyl alcohol polyglycol ether (10 EO) R—O—[CH₂CH₂O]₁₀H |
| Genapol O 109 | oleyl alcohol polyglycol ether (10 EO) R—O—[CH₂CH₂O]₁₀H |
| Genapol O 120 | oleyl alcohol polyglycol ether (12 EO) R—O—[CH₂CH₂O]₁₂H |
| Genapol O 150 | oleyl alcohol polyglycol ether (15 EO) R—O—[CH₂CH₂O]₁₅H |
| Genapol O 200 | oleyl alcohol polyglycol ether (20 EO) R—O—[CH₂CH₂O]₂₀H |
| Genapol O 230 | oleyl alcohol polyglycol ether (23 EO) R—O—[CH₂CH₂O]₂₃H |
| Genapol O 300 | oleyl alcohol polyglycol ether (30 EO) R—O—[CH₂CH₂O]₃₀H | and in the foregoing, R is a monounsaturated oleyl alcohol, and wherein a monounsaturation is at or near the midpoint from the terminal ends of the oleyl alcohol.

A particularly preferred R residue is based on oleyl alcohol which has a structure: $CH_3(CH_2)_7$—$CH=CH$—$(CH_2)_8$—$OH$, and contains a single monounsaturation at or near the midpoint from the terminal ends of the fatty alcohol.

Further preferred fatty alcohol glycol ethers of the foregoing structural formula (I) include those which are presently commercially available in the Genapol® "U" series of nonionic surfactants as well. Nonlimiting examples of such include: Genapol® U 100 described to be a $C_{14/16/18}$ alkyl ethoxylate with 10 EO, $C_{14/16/18}$ alcohol, unsaturated, and Genapol® U 200 described to be a $C_{14/16/18}$ alkyl ethoxylate with 20 EO, $C_{14/16/18}$ alcohol, unsaturated.

Advantageously the adhesion promoter based on a fatty alcohol polyglycol ether is present in the compositions in amount of from about 50% wt. to about 50% wt., preferably from about 20% wt. to about 45% wt. based on the total weight of the lavatory treatment compositions of which they form a part. The identity of especially preferred adhesion promoters and their content within the lavatory treatment compositions of the devices according to the invention are disclosed with reference to one or more of the example compositions.

A next essential constituent of the lavatory treatment compositions is an organic solvent constituent which is liquid at room temperature (20° C.). The organic solvent constituent compositions comprise one or more organic solvents as the organic solvent constituent, but in preferred embodiments is a single organic solvent. By way of non-limiting example exemplary useful organic solvents which are liquid at room temperature (20° C.) and which may be included in the lavatory treatment compositions are those which are at least partially water-miscible such as alcohols (e.g., low molecular weight alcohols, such as, for example, ethanol, propanol, isopropanol, and the like), glycols (such as, for example, ethylene glycol, propylene glycol, hexylene glycol, and the like), water-miscible ethers (e.g. diethylene glycol diethylether, diethylene glycol dimethylether, propylene glycol dimethylether), water-miscible glycol ether (e.g. propylene glycol monomethylether, propylene glycol mono ethylether, propylene glycol monopropylether, propylene glycol monobutylether, ethylene glycol monobutylether, dipropylene glycol monomethylether, diethyleneglycol monobutylether), lower esters of monoalkylethers of ethylene glycol or propylene glycol (e.g. propylene glycol monomethyl ether acetate), and mixtures thereof. Glycol ethers having the general structure $R_a$—$R_b$—OH, wherein $R_a$ is an alkoxy of 1 to 20 carbon atoms, or aryloxy of at least 6 carbon atoms, and $R_b$ is an ether condensate of propylene glycol and/or ethylene glycol having from one to ten glycol monomer units are among the preferred organic solvents. Polyhydroxy organic solvents, viz, those having two or more —OH moieties are in certain cases, also preferred for use.

The organic solvent may also be one or more further liquids such as glycerine and paraffin oil, as well as petroleum distillates and/or petroleum products, paraffinic oils usually based on n-alkanes, naphthenic oils usually based on cycloalkanes, aromatic oils such as those based on aromatic hydrocarbons, mineral oil, as well as technical grade mixtures of hydrocarbons may be used as or in the organic solvent. Examples of the latter include paraffinic hydrocarbons including both linear and branched paraffinic hydrocarbons; the former are commercially available as NORPAR solvents (ex. ExxonMobil Corp.) while the latter are available as ISOPAR solvents (ex. ExxonMobil Corp.) Mixtures of branched hydrocarbons especially as isoparaffins form are also contemplated to be useful.

In certain preferred embodiments the organic solvent constituent necessarily comprises (or consists essentially of, or consists of) at least one glycol or glycol ether, and further includes one or both of glycerine and/or mineral oil. When such at least one glycol or glycol ether is present in conjunction with one or both of glycerine and/or mineral oil, preferably the mass of the at least one glycol or glycol ether is at least about three times, preferably at least about four times that of the total mass of the glycerine and/or a mineral oil present.

In other preferred embodiments the organic solvent constituent necessary comprises (or consists essentially of, or consists of) glycerine and mineral oil, and further preferably the mass of the glycerine is at least about least about three times, preferably at least about four times that of the total mass of the mineral oil present.

In certain preferred embodiments the organic solvent constituent consists essentially of, yet more preferably consists of, at least one polyhydroxy organic solvents, e.g., a glycol or glycol ether, and further includes one or both of glycerine and/or mineral oil.

In further, certain preferred embodiments the organic solvent constituent consists essentially of, yet more preferably consists of, at least one glycol or glycol ether, and mineral oil.

In further, certain preferred embodiments the organic solvent constituent consists essentially of, yet more preferably consists of, at least one glycol or glycol ether, and both glycerine and mineral oil.

In further, certain preferred embodiments the organic solvent constituent consists essentially of, yet more preferably consists of, glycerine and mineral oil.

The organic solvent constituent comprises 1-25% wt. of the lavatory treatment compositions. Preferably, in order of increasing preference, the organic solvent constituent is present in an amount of at least about 0.01%, 0.1%, 0.5%, 0.75%. 1%. 1.25%, 1.5%, 1.75%, 2%, 2.25%, 2.5%, 2.75%, 3%, 3.25%, 3.5%, 3.75%, 4%, 4.25%, 4.5%, 4.75%, 5%, 5.25%, 5.5%, 5.75%, 6%, 6.25%, 6.5%, 6.75%, 7%, 7.25%, 7.5%, 7.75%, 8%, 8.25%, 8.5%, 8.75%, and 9% wt. of the lavatory treatment composition of which they form a part. Preferably, in order of increasing preference, the organic solvent constituent comprises not more than about 25%, 20%, 18%, 17%, 16%, 15%, 14.5%, 14%, 13.5%, 13%, 12.5%, 12%, 11.5%, 11%, 10.75%, 10.5%, 10.25%, 10%, 9.75%, 9.5%, 9.25%, 9%, 8.75%, 8.5%, 8.25%, 8%, 7.75%, 7.5%, 7.25%, 7%, 6.75%, 6.5%, 6.25%, 6%, 5.75%, 5.5%, 5.25%, 5%, 4.75%, 4.5%, 4.25%, 4%, 3.75%, 3.5%, 3.25%, 3%, 2.75%, 2.5%, 2.25%, 2%, 1.75%, 1.5%, 1.25% and 1% wt. of the lavatory treatment composition of which they form a part. Particularly preferred amounts of the organic solvent constituent are recited in one or more of the Examples, with preferred ranges of the organic solvent constituent also disclosed in the Examples.

In certain preferred embodiments, within the lavatory treatment compositions:

(a) the ratio (in % wt.) of polyhydroxy organic solvent: other solvents of the organic solvent constituent is in the range of about 4-12:1, preferably about 4.5-10:1, and especially preferably 4.5-8.5:1; and/or, (b) the ratio (in % wt.) of polyhydroxy organic solvent: mineral oil is in the range of about 5-20:1, more preferably about 7:18:1; and/or, (c) the ratios (in % wt.) of water:organic solvent constituent is in the range of about 5-20:1, more preferably about 6-16:1; and/or, (d) the ratios (in % wt.) of water:polyhydroxy organic solvent constituent is in the range of about 5-25:1, preferably about 7-25:1.

Particular and preferred specific ratios of (a), (b), (c) and/or (d) are disclosed with reference to one or more of the examples.

In certain particularly preferred embodiments of the lavatory treatment compositions, the conditions outlined of at least two of, preferably at least three of, and particularly preferably the conditions outlined in all four of (a), (b), (c) and (d) are met/satisfied.

A next essential constituent of the lavatory treatment compositions is at least one detersive surfactant constituent. As the detersive surfactant constituent there may be used one or more anionic, cationic, nonionic, amphoteric or zwitterionic surfactant compounds. Especially preferred surfactants of the surfactant constituent are disclosed with reference to the examples.

Exemplary useful anionic surfactants include the water-soluble salts, particularly the alkali metal, ammonium and alkylolammonium (e.g., monoethanolammonium or triethanolammonium) salts, of organic sulfuric reaction products having in their molecular structure an alkyl group containing from about 10 to about 20 carbon atoms and a sulfonic acid or sulfuric acid ester group. (Included in the term "alkyl" is the alkyl portion of aryl groups.) Examples of this group of synthetic surfactants are the alkyl sulfates, especially those obtained by sulfating the higher alcohols ($C_8$-$C_{18}$ carbon atoms) such as those produced by reducing the glycerides of tallow or coconut oil; and the alkylbenzene sulfonates in which the alkyl group contains from about 9 to about 15 carbon atoms, in straight chain or branched chain. Exemplary useful are linear straight chain alkylbenzene sulfonates in which the average number of carbon atoms in the alkyl group is from about 11 to 14.

Other exemplary useful anionic surfactants herein are the water soluble salts of: paraffin sulfonates containing from about 8 to about 24 (preferably about 12 to 18) carbon atoms; alkyl glyceryl ether sulfonates, especially those ethers of $C_{8-18}$ alcohols (e.g., those derived from tallow and coconut oil); alkyl phenol ethylene oxide ether sulfates containing from about 1 to about 4 units of ethylene oxide per molecule and from about 8 to about 12 carbon atoms in the alkyl group; and alkyl ethylene oxide ether sulfates containing about 1 to about 4 units of ethylene oxide per molecule and from about 10 to about 20 carbon atoms in the alkyl group.

Other useful anionic surfactants herein include the water soluble salts of esters of α-sulfonated fatty acids containing from about 0 to 20 carbon atoms in the fatty acid group and from about 1 to 10 carbon atoms in the ester group; water soluble salts of 2-acyloxy-alkane-1-sulfonic acids containing from about 2 to 9 carbon atoms in the acyl group and from about 9 to about 23 carbon atoms in the alkane moiety; water-soluble salts of olefin sulfonates containing from about 12 to 24 carbon atoms; and β-alkyloxy alkane sulfonates containing from about 1 to 3 carbon atoms in the alkyl group and from about 8 to 20 carbon atoms in the alkane moiety.

Further exemplary useful as anionic surfactants are carboxylates such as alkyl carboxylates which include those which may be represented by the general formula:

wherein R is a straight or branched hydrocarbon chain containing from about 9 to 21 carbon atoms, and M is a metal or ammonium ion; polyalkoxycarboxylates, representative of which are polyethoxycarboxylates which may be represented by the general formula:

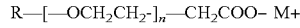

wherein R is a straight chained or branched hydrocarbon chain which may include an aryl moiety, but is desirably a straight chained or branched hydrocarbon chain; and n is an integer value of from 1-24.

In certain embodiments of the invention, one or more anionic surfactants are excluded from the lavatory treatment compositions of the invention.

Exemplary useful cationic surfactants include quaternary ammonium compounds and salts thereof which may include quaternary ammonium germicides characterized by the general structural formula:

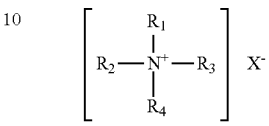

where at least one or $R_1$, $R_2$, $R_3$ and $R_4$ is a alkyl, aryl or alkylaryl substituent of from 6 to 26 carbon atoms, and desirably the entire cation portion of the molecule has a molecular weight of at least 165. The alkyl substituents may be long-chain alkyl, long-chain alkoxyaryl, long-chain alkylaryl, halogen-substituted long-chain alkylaryl, long-chain alkylphenoxyalkyl, arylalkyl, etc. The remaining substituents on the nitrogen atoms other than the abovementioned alkyl substituents are hydrocarbons usually containing no more than 12 carbon atoms. The substituents $R_1$, $R_2$, $R_3$ and $R_4$ may be straight-chained or may be branched, but are preferably straight-chained, and may include one or more amide, ether or ester linkages. The counterion X may be any salt-forming anion which permits water solubility of the quaternary ammonium complex. Exemplary counterions include halides, for example chloride, bromide or iodide, or methosulfate.

Exemplary quaternary ammonium salts within the above description include the alkyl ammonium halides such as cetyl trimethyl ammonium bromide, alkyl aryl ammonium halides such as octadecyl dimethyl benzyl ammonium bromide, N-alkyl pyridinium halides such as N-cetyl pyridinium bromide, and the like. Other suitable types of quaternary ammonium salts include those in which the molecule contains either amide, ether or ester linkages such as octyl phenoxy ethoxy ethyl dimethyl benzyl ammonium chloride, N-(laurylcocoaminoformylmethyl)-pyridinium chloride, and the like. Other very effective types of quaternary ammonium compounds which are useful as germicides include those in which the hydrophobic radical is characterized by a substituted aromatic nucleus as in the case of lauryloxyphenyltrimethyl ammonium chloride, cetylaminophenyltrimethyl ammonium methosulfate, dodecylphenyltrimethyl ammonium methosulfate, dodecylbenzyltrimethyl ammonium chloride, chlorinated dodecylbenzyltrimethyl ammonium chloride, and the like.

Preferred quaternary ammonium compounds which act as germicides and which are be found useful in the practice of the present invention include those which have the structural formula:

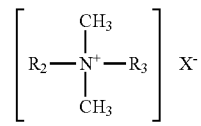

wherein $R_2$ and $R_3$ are the same or different $C_8$-$C_{12}$ alkyl, or $R_2$ is $C_{12-16}$ alkyl, $C_{8-18}$ alkylethoxy, $C_{8-18}$ alkylphenolethoxy and $R_3$ is benzyl, and X is a halide, for example chloride, bromide or iodide, or methosulfate. The alkyl groups recited in $R_2$ and $R_3$ may be straight-chained or branched, but are preferably substantially linear. The counterion X is as described previously.

As further preferred cationic surfactant constituents are those materials presently commercially available in the Suga®Quat series of materials, which include at least those materials presently commercially available as: Suga®Quat L-1010, described as being laurdimoniumhydroxypropyl decylglucosides chloride; Suga®Quat L-1210, described as being laurdimoniumhydroxypropyl laurylglucosides chloride; Suga®Quat S-1010, described as being stearyldimoniumhydroxypropyl decylglucosides chloride; Suga®Quat S-1210, described as being stearyldimoniumhydroxypropyl laurylglucosides chloride; Suga®Quat S-1218, described as being stearyldimoniumhydroxypropyl laurylglucosides chloride; and Suga®Quat TM-8310, described as being cocoglucosides hydroxypropyltrimonium chloride. All of the foregoing are presently commercially available from ex. Colonial Chemical, Inc. (South Pittsburgh, Tenn. (USA)). Exemplary useful Suga®Quat series of materials include those as described in U.S. Pat. No. 6,881,710 (the contents of which are incorporated by reference), which are materials which conform to one or both of the following structures (a) and/or (b):

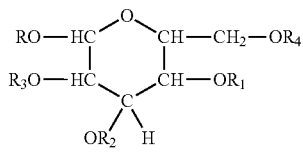

(a)

in which:
R is $C_8$-$C_{22}$ alkyl;
$R_1$, $R_2$, $R_3$ and $R_4$ are independently selected from the group consisting of: H, and the further group,

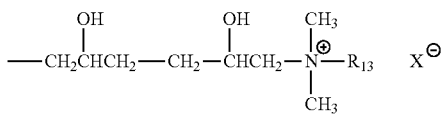

in which $R_{13}$ is $C_8$-$C_{22}$ alkyl with the proviso that $R_1$, $R_2$, $R_3$ and $R_4$ are not all H;
and X is a halogen, preferably Cl, Br or I,

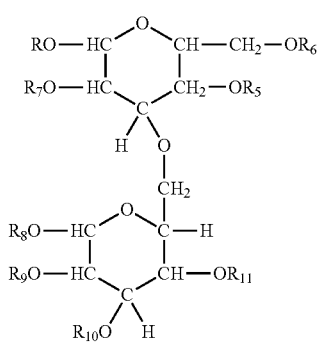

(b)

in which:
R is $C_8$-$C_{22}$ alkyl;
$R_5$, $R_6$, $R_7$, $R_8$, $R_9$, $R_{10}$ and $R_{11}$ are independently selected from the group consisting of: H, and the further group,

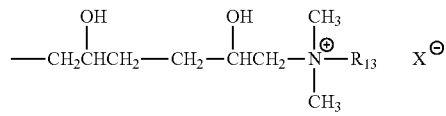

in which $R_{13}$ is $C_8$-$C_{22}$ alkyl, with the proviso that $R_5$, $R_6$, $R_7$, $R_8$, $R_9$, $R_{10}$ and $R_{11}$ are not all H;
and X is a halogen, preferably Cl, Br or I.

The foregoing materials according to structures (a) and/or (b) are generally provided as aqueous compositions comprising about 35% wt. of one or more of the said foregoing compounds according to formula (a) and/or (b) and the balance being substantially water.

Of the foregoing materials according to formula (a) or (b), particularly preferred are those which generally conform to the following structure:

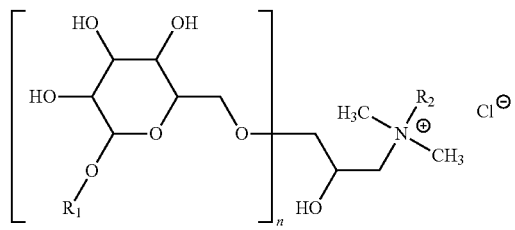

in which: n has a value of 1 or more, and $R_1$ and $R_2$ are carbon containing moieties.

A further preferred cationic surfactant is alkyl hydroxyethyl dimethyl ammonium chloride, commercially available as Praepagen® HEQ-10 (ex. Clariant).

In certain embodiments of the invention, one or more cationic surfactants are excluded from the lavatory treatment compositions of the invention.

In certain preferred embodiments of the invention, the detersive surfactant constituent comprises (or consists essentially of, or consists of) one or more cationic surfactants.

Exemplary useful nonionic surfactants, include known art nonionic surfactant compounds. Practically any hydrophobic compound having a carboxy, hydroxy, amido, or amino group with a free hydrogen attached to the nitrogen can be condensed with ethylene oxide or with the polyhydration product thereof, polyethylene glycol, to form a water soluble nonionic surfactant compound. Further, the length of the polyethylenoxy hydrophobic and hydrophilic elements may various. Exemplary nonionic compounds include the polyoxyethylene ethers of alkyl aromatic hydroxy compounds, e.g., alkylated polyoxyethylene phenols, polyoxyethylene ethers of long chain aliphatic alcohols, the polyoxyethylene ethers of hydrophobic propylene oxide polymers, and the higher alkyl amine oxides. Alkoxylated alkyl phenols including those commercially available under the tradename Triton® X series (Union Carbide Chem. Co., Danbury Conn.) may be advantageously added.

Further nonionic surfactants which may be optionally present in the inventive composition are alkyl polyglycoside. Suitable alkyl polyglycosides are known nonionic surfactants which are alkaline and electrolyte stable. Alkyl mono and polyglycosides are prepared generally by reacting a monosaccharide, or a compound hydrolyzable to a monosaccharide with an alcohol such as a fatty alcohol in an acid medium. Various glycoside and polyglycoside compounds including alkoxylated glycosides and processes for making them are disclosed in U.S. Pat. No. 2,974,134; U.S. Pat. No. 3,219,656; U.S. Pat. No. 3,598,865; U.S. Pat. No. 3,640,998; U.S. Pat. No. 3,707,535; U.S. Pat. No. 3,772,269; U.S. Pat. No. 3,839,318; U.S. Pat. No. 3,974,138; U.S. Pat. No. 4,223,129; and U.S. Pat. No. 4,528,106.

A preferred group of alkyl glycoside surfactants suitable for use in the practice of this invention may be represented by formula I below:

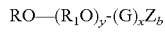

wherein:
R is a monovalent organic radical containing from about 6 to about 30,
preferably from about 8 to about 18 carbon atoms;
$R_1$ is a divalent hydrocarbon radical containing from about 2 to about 4 carbon atoms;
O is an oxygen atom;
y is a number which has an average value from about 0 to about 1 and is preferably 0;
G is a moiety derived from a reducing saccharide containing 5 or 6 carbon atoms; and
x is a number having an average value from about 1 to 5 (preferably from 1.1 to 2);
Z is $O_2M^1$,

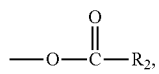

$O(CH_2)$, $CO_2M^1$, $OSO_3M^1$, or $O(CH_2)SO_3M^1$; $R_2$ is $(CH_2)CO_2M^1$ or $CH=CHCO_2M^1$; (with the proviso that Z can be $O_2M^1$ only if Z is in place of a primary hydroxyl group in which the primary hydroxyl-bearing carbon atom,
—$CH_2OH$, is oxidized to form a

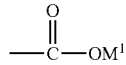

group);
b is a number of from 0 to 3x+1 preferably an average of from 0.5 to 2 per glycosal group;
p is 1 to 10,
$M^1$ is $H^+$ or an organic or inorganic cation, such as, for example, an alkali metal, ammonium, monoethanolamine, or calcium.

As defined in Formula I above, R is generally the residue of a fatty alcohol having from about 8 to 30 and preferably 8 to 18 carbon atoms. Examples of such alkylglycosides as described above include, for example, APG™ 325 CS GLYCOSIDE which is described as being a 50% $C_9$-$C_{11}$ alkyl polyglycoside, also commonly referred to as D-glucopyranoside, (commercially available from Henkel Corp, Ambler Pa.) and GLUCOPON™ 625 CS which is described as being a 50% $C_{10}$-$C_{16}$ alkyl polyglycoside, also commonly referred to as a D-glucopyranoside.

A further class of exemplary useful nonionic surfactants include nonionic surfactant compounds which are based on a polymeric alkylene oxide block copolymer. Polymeric alkylene oxide block copolymers include nonionic surfactants in which the major portion of the molecule is made up of block polymeric $C_2$-$C_4$ alkylene oxides. Such nonionic surfactants, while preferably built up from an alkylene oxide chain starting group, and can have as a starting nucleus almost any active hydrogen containing group including, without limitation, amides, phenols, thiols and secondary alcohols. One preferred class of such nonionic surfactants containing the characteristic alkylene oxide blocks are those which may be generally represented by the formula (A):

where
EO represents ethylene oxide,
PO represents propylene oxide,
y equals at least 15,
$(EO)_{x+z}$ equals 20 to 50% of the total weight of said compounds, and, the total molecular weight is preferably in the range of about 2000 to 15,000.

Examples of further and particularly useful nonionic surfactant compounds which include as a major portion of the molecule a block polymeric alkylene oxide block are those materials presently commercially available under the tradename "Pluronic®", and in particular the Pluronic®F series, Pluronic®L series, Pluronic®P series, as well as in the Pluronic®R series, each of which are generally described to be block copolymers of propylene oxide and ethylene oxide, and are presently commercially available from BASF AG (Ludwigshafen, Germany) as well as from BASF Corp. (Mt. Olive Township, N.J.).

In certain embodiments of the invention, one or more nonionic surfactants are excluded from the lavatory treatment compositions of the invention.

Exemplary useful amphoteric surfactants include alkylbetaines, particularly those which may be represented by the following structural formula:

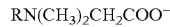

wherein R is a straight or branched hydrocarbon chain which may include an aryl moiety, but is preferably a straight hydrocarbon chain containing from about 6 to 30 carbon atoms. Further exemplary useful amphoteric surfactants include amidoalkylbetaines, such as amidopropylbetaines which may be represented by the following structural formula:

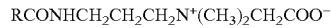

wherein R is a straight or branched hydrocarbon chain which may include an aryl moiety, but is preferably a straight hydrocarbon chain containing from about 6 to 30 carbon atoms. Further useful amphoteric surfactants include sultaines, including compounds which may be represented by the following formula:

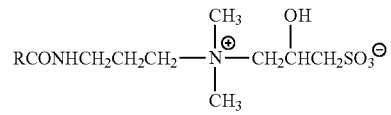

In the above formulae, R represents a $C_8$ to $C_{24}$ alkyl group, and is preferably a $C_{10}$ to $C_{16}$ alkyl group.

In certain embodiments of the invention, one or more amphoteric surfactants and/or zwitterionic surfactants are excluded from the lavatory treatment compositions of the invention.

Further exemplary surfactants include sarcosinate surfactants which are alkali metal salts of N-alkyl-N-acyl amino acids. These are salts derived from the reaction of (1) N-alkyl substituted amino acids of the formula:

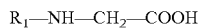

where $R_1$ is a linear or branched chain lower alkyl of from 1 to 4 carbon atoms, especially a methyl, for example, aminoacetic acids such as N-methylaminoacetic acid (i.e. N-methyl glycine or sarcosine), N-ethyl-aminoacetic acid, N-butylaminoacetic acid, etc., with (2) saturated natural or synthetic fatty acids having from 8 to 18 carbon atoms, especially from 10 to 14 carbon atoms, e.g. lauric acid, and the like.

The resultant reaction products are salts which may have the formula:

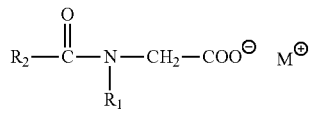

where M is an alkali metal ion such as sodium, potassium or lithium; $R_1$ is as defined above; and wherein $R_2$ represents a hydrocarbon chain, preferably a saturated hydrocarbon chain, having from 7 to 17 carbon atoms, especially 9 to 13 carbon atoms of the fatty acyl group

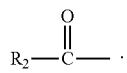

Exemplary useful sarcosinate surfactants include cocoyl sarcosinate, lauroyl sarcosinate, myristoyl sarcosinate, palmitoyl sarcosinate, stearoyl sarcosinate and oleoyl sarcosinate, and tallow sarcosinate. Such materials are also referred to as N-acyl sarcosinates.

In certain embodiments of the invention, one or more sarcosinate surfactants are excluded from the lavatory treatment compositions of the invention.

The surfactant constituent comprises from about 0.5% wt. to about 35% wt., preferably from about 5% wt. to about 25% wt. of the lavatory treatment compositions, based on the said compositions of which they form a part. Preferred surfactant compounds are ones which provide good foaming and cleaning characteristics to the lavatory treatment compositions described herein.

The identity of especially preferred surfactants and of the surfactant constituent of the lavatory treatment compositions of the invention are disclosed with reference to one or more of the example compositions.

Water is an essential constituent and comprises between about 25% wt. and 75% wt., preferably about 30% wt. and about 60% wt. of the lavatory treatment compositions of the invention. The water may be tap water, but is preferably distilled and is most preferably deionized water. If the water is tap water, it is preferably substantially free of any undesirable impurities such as organics or inorganics, especially minerals salts which are present in hard water which may thus undesirably interfere with the operation of the constituents present in the compositions according to the invention.

Preferably, the amount of water added to the compositions is advantageously sufficient to ensure that the resultant lavatory treatment compositions are self-supporting gels, which do not appreciably sag or run.

More desirably the lavatory treatment compositions of the invention are "ringing gels". These ringing gels do not appreciably sag or run when formed, and are amorphous, non-crystalline materials which exhibit a ringing phenomena when they are excited by mechanical vibrations. Such ringing gels are believed to be microemulsion gels which are formed by the incorporation of the dispersed organic solvent constituent within the water, adhesion promoter constituent and the detersive surfactant constituent which form the bulk of the lavatory treatment compositions of the invention.

In certain preferred embodiments the lavatory treatment compositions of the invention are ringing gels, which form within 48 hours of being mixed, preferably within 24 hours of being mixed.

The inventive compositions preferably and in some embodiments necessarily further comprise a co-adhesion promoter constituent based on one or more oxyalkylenated compounds. These oxyalkylenated compound(s) typically comprise ethylene oxide groups ("EO") (oxyethylenated compounds), or propylene oxide groups ("PO") (oxypropylenated compounds) or both ("EO/PO") (oxyethylenated/oxypropylenated compounds). Of course, a plurality of oxyalkylenated compound(s) may be used in the primary adhesion promoter constituent of the adhesive lavatory treatment compositions.

Exemplary suitable oxyalkylenated compounds may be selected from: polyethylene glycols, polyethylene glycol esters and/or polypropylene glycol esters, polyethylene glycol ethers and/or polypropylene glycol ethers, alkoxylated acyl derivatives, ethoxylated acyl polyol derivatives, oxyalkylenated (especially) oxyethylenated triesters of glycerol and of fatty acids, and mixtures thereof.

Non-limiting examples of suitable polyethylene glycols which may be used in the composition of the invention include ethylene oxide polycondensates having a number of ethylene oxide (EO) units of greater than 10, and preferably greater than about 20. The ethylene oxide number preferably range from about 10 to about 50,000 and preferably from about 20 to about 10,000. Non-limiting examples of such polyethylene glycols include polyethylene glycol comprising 7,000 EO (CTFA name: PEG-7M), polyethylene glycol comprising 75 EO (CTFA name: PEG-75), polyethylene glycol comprising 20,000 EO (CTFA name: PEG-20M), and polyethylene glycol comprising 150 EO (CTFA name: PEG-150).

Non-limiting examples of suitable polyethylene glycol esters and/or polypropylene glycol esters include condensates of polyethylene glycol and/or polypropylene glycol with one or more fatty acids. These compounds typically have the formula:

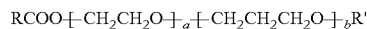

wherein:
each of R and R' independently represent: hydrogen or a saturated or unsaturated, linear or branched, hydroxylated or non-hydroxylated alkyl chain containing from 1 to 30 carbon atoms, preferably from 12 to 22 carbon atoms, or an aryl chain, with the proviso that R and R' are not simultaneously hydrogen,
a=0-300
b=0-300, and preferably a+b is greater than or equal to 10, preferably at least 20, still more preferably at least 30.

Non-limiting examples of polyethylene glycol acid esters and/or polypropylene glycol acid esters include polyethylene glycol distearate (150 EO), PEG-150 dibehenate, polyethylene glycol palmitostearate (120 EO), the copolymer of polyethylene glycol (30 EO) and of 12-hydroxystearic acid, and polyethylene glycol stearate (40 EO). Examples of compounds according to the foregoing formula wherein R and R' are both hydrogen, such compound may be polyoxyethylene polyoxypropylene copolymers.

Non-limiting examples of polyethylene glycol ethers and/or polypropylene glycol ethers include condensates of polyethylene glycol and/or polypropylene glycol with one or more fatty alcohols. These compounds typically conform to the formula:

$$RCOO\text{-}[CH_2CH_2O]_a\text{-}[CH_2CH_2CH_2O]_b\text{-}R'$$

wherein:
each of R and R' represent, independently of each other, hydrogen or a saturated or unsaturated, linear or branched, hydroxylated or non-hydroxylated alkyl chain containing from 1 to 30 carbon atoms, preferably from 12 to 22 carbon atoms, or an aryl chain, with the proviso that R and R' are not simultaneously hydrogen.
a=0-300
b=0-300, and preferably a+b is greater than or equal to 10, preferably at least 20, still more preferably at least 30.

Non-limiting examples of such polyethylene glycol ethers include oxyethylenated (30 EO) cetyl alcohol, oxyethylenated (15 EO) oleyl alcohol, oxyethylenated (50 EO) oleyl alcohol, oxyethylenated (10 EO) behenyl alcohol, oxyethylenated (30 EO) behenyl alcohol, oxyethylenated (12 EO) lauryl alcohol, oxyethylenated (23 EO) lauryl alcohol, oxyethylenated (20 EO) 2-octyldodecyl alcohol, oxyethylenated (20 EO) isocetyl alcohol, oxyethylenated (10 EO) oleyl alcohol, oxyethylenated (20 EO) oleyl alcohol, oxyethylenated (100 EO) stearyl alcohol, and oxyethylenated (21 EO) stearyl alcohol.

Non-limiting examples of polyethylene glycol/polypropylene glycol ethers in particular, include oxyethylenated (5 EO) oxypropylenated (5 PO) lauryl alcohol, oxypropylenated (3 PO) myristyl alcohol, oxyethylenated (20 EO) oxypropylenated (5 PO) cetyl alcohol, oxyethylenated (26 EO) oxypropylenated (26 PO) butyl alcohol, oxyethylenated (26 EO) oxypropylenated (26 PO) butyl alcohol, oxyethylenated (30 EO) oxypropylenated (6 PO) decyltetradecanol, and oxyethylenated (25 EO) oxypropylenated (25 PO) lauryl alcohol.

Non-limiting examples of ethoxylated alkyl or aryl derivatives of polyol include oxyethylenated derivatives of fatty acid esters or of fatty alcohol ethers and of a polyol such as glycerol, sorbitol, glucose or pentaerythritol. Suitable derivatives of this type include, for example, oxyethylenated (78 EO) glyceryl cocoate, oxyethylenated (120 EO) methylglucose dioleate, oxyethylenated (40 EO) sorbitan septaoleate, oxyethylenated (10 EO) polyglyceryl (2 mol of glycerol) laurate, oxyethylenated (60 EO) glyceryl isostearate, oxyethylenated (20 EO) glyceryl monostearate, oxyethylenated (200 EO) glyceryl stearate, and oxyethylenated (150 EO) pentaerythrityl tetrastearate, such as the product sold under the name Crothix™. (ex. Croda, Inc.)

Non-limiting examples of suitable oxyalkylenated glyceryl triesters of fatty acids include, for example, oxyethylenated (6 EO) caprylic/capric acid glycerides, and oxyethylenated (50 EO) olive oil.

Particularly preferred for use in the co-adhesion promoter constituent are compounds according to the structure:

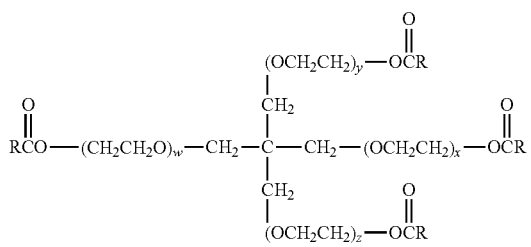

wherein,
R is a fatty acid moiety, preferably a stearic fatty acid moiety, and the sum of w+x+y+z is in the range of 50-1500, preferably in the range of 70-500, more preferably in the range of about 100-350 and especially preferably about 150.

A particularly preferred primary adhesion promoter constituent is a material presently commercially available under the tradename Crothix (ex. Croda, Inc.).

Further particularly preferred co-adhesion promoters include high molecular weight water-soluble poly(ethylene oxide) polymers, which desirably have molecular weights (weight average) in the range from about 100,000 to about 8,000,000. Such high molecular weight water-soluble poly(ethylene oxide) polymers are presently commercially available as Polyox resins (ex. Dow Chem. Co.).

In certain embodiments, the co-adhesion promoter constituent is pasty or is solid at room temperature (20° C.).

Mixtures of two or more of the foregoing materials and/or compounds may be used to provide the co-adhesion promoter constituent. Alternatively a single of the foregoing materials and/or compounds can be used to provide the co-adhesion promoter constituent.

In certain preferred embodiments, one or more of the foregoing co-adhesion promoters are expressly excluded from the adhesive lavatory treatment compositions.

In further preferred embodiments a co-adhesion promoter is necessarily present in the adhesive lavatory treatment compositions.

When present, the co-adhesion promoter constituent comprises from about 0.001% wt.-5% wt., preferably about 0.05% wt.-2.5% wt., based on the total weight of the inventive composition of which it forms a part.

In embodiments of the invention, wherein both a primary adhesion promoter and a co-adhesion promoter are concurrently present, preferably the weight ratio of the former to the latter is at least about not more than 10:1, and especially preferably is not more than about 20:1

The identity of especially preferred co-adhesion promoter constituents and their content within lavatory treatment compositions of the invention are disclosed with reference to one or more of the Example compositions.

Optionally the lavatory treatment compositions of the invention may comprise one or more further optional constituents which may impart a further aesthetic or technical benefit to the said lavatory treatment compositions. When present, such further optional constituents are generally present in a cumulative amount of less than about 25% wt. based on the total weight of the lavatory treatment compositions wherein one or more such further optional constituents may be present. By way of non-limiting example such further optional constituents include one or more of: coloring agents, fragrances and fragrance solubilizers, viscosity modifying agents, thickeners, bleaches, bleach releasing compounds, oxidizing agents, germicidal agents, pH adjusting agents and pH buffers including organic and inorganic salts as well as organic and inorganic acids, builders, chelating agents, opacifying agents, titanium dioxide, inert inorganic or organic fillers, visually discernible additive materials, hydrotropes, enzymes as well as other biologically active constituents, anti-oxidants, preservatives, and anti-corrosion agents, as well as other optional constituents known to the skilled artisan. When one or more of the optional constituents is added, i.e., fragrance and/or coloring agents, the esthetic and consumer appeal of the lavatory treatment forming part of the lavatory treatment device is often favorably improved. The use and selection of these optional constituents should be based on imparting a desired additional aesthetic or technical benefit, as well as to ensure compatibility with the further constituents present in the lavatory treatment compositions, especially such that any desirable properties of the lavatory treatment compositions are not deleteriously diminished.

Optionally the lavatory treatment compositions may further comprise a germicide constituent (other than cationic germicidally active quaternary ammonium halide surfactants noted above) which has germicidal or antimicrobial efficacy against at least one of gram-positive or gram-negative pathogens, e.g., bacteria or other microorganisms. Such may be based, for example, on one or more non-cationic antimicrobial compounds or constituents, e.g., halophenols such 3-trifluoromethyl-4,4'-dichlorocarbanilide, 3,3',4-trichlorocarbanilide, as well as 2,4-dichloro-3,5-m-xylenol ("DCMX"). The phenol based non-cationic antimicrobials are preferred, of which parachlorometacresol ("PCMC") and especially parachlorometaxylenol ("PCMX").

Alternately such may be based, for example, on one or more phenol derivatives such as those based on 2-hydroxydiphenyl compounds, including Triclosan® (ex. Ciba), those based on 2,2'-hydroxy-5,5'-dibromo-diphenyl ethers, such as one or more of chlorophenols (o-, m-, p-), 2,4-dichlorophenol, p-nitrophenol, picric acid, xylenol, p-chloro-m-xylenol, cresols (o-, m-, p-), p-chloro-m-cresol, pyrocatechol, resorcinol, 4-n-hexylresorcinol, pyrogallol, phloroglucin, carvacrol, thymol, p-chlorothymol, o-phenylphenol, o-benzylphenol, p-chloro-o-benzylphenol, phenol, 4-ethylphenol, and 4-phenolsulfonic acid, as well as further diphenol compounds such as hexachlorophene, tetrachlorophene, dichlorophene, 2,3-dihydroxy-5,5'-dichlorodiphenyl sulfide, 2,2'-dihydroxy-3,3',5,5'-tetrachlorodiphenyl sulfide, 2,2'-dihydroxy-3,5',5,5',6,6'-hexachlorodiphenyl sulfide, and 3,3'-dibromo-5,5'-dichloro-2,2'-dihydroxydiphenylamine, and especially "Triclocarban", 3,4,4'-trichlorocarbanilide as well as derivatives thereof.

The optional germicide constituent may also be based on one or more acids, including organic acids such as salicylic and citric acid, and/or inorganic acid such as hydrochloric acid when present in effective amounts in order to sufficiently acidify the lavatory treatment composition.

Optionally the lavatory treatment compositions may comprise a preservative constituent. Such preservatives are primarily included to reduce the growth of undesired microorganisms within the lavatory treatment device during storage prior to use. Exemplary useful preservatives include compositions which include parabens, including methyl parabens and ethyl parabens, glutaraldehyde, formaldehyde, 2-bromo-2-nitropropoane-1,3-diol, 5-chloro-2-methyl-4-isothiazolin-3-one, 2-methyl-4-isothiazoline-3-one, and mixtures thereof. One exemplary composition is a combination 5-chloro-2-methyl-4-isothiazolin-3-one and 2-methyl-4-isothiazolin-3-one where the amount of either component may be present in the mixture anywhere from 0.001 to 99.99 weight percent, based on the total amount of the preservative. Further exemplary useful preservatives include those which are commercially including a mixture of 5-chloro-2-methyl-4-isothiazolin-3-one and 2-methyl-4-isothiazolin-3-one marketed under the trademark KATHON® CG/ICP as a preservative composition presently commercially available from Rohm and Haas (Philadelphia, Pa.). Further useful and commercially available preservative compositions include KATHON® CG/ICP II, a further preservative composition presently commercially available from Rohm and Haas (Philadelphia, Pa.), PROXEL® which is presently commercially available from Zeneca Biocides (Wilmington, Del.), SUTTOCIDE® A which is presently commercially available from Sutton Laboratories (Chatam, N.J.) as well as TEXTAMER® 38AD which is presently commercially available from Calgon Corp. (Pittsburgh, Pa.). An exemplary and preferred preservative is 1,3-bis(hydroxymethyl)5,5-dimethylimidazolidine-2,4-dione, which is presently commercially available as NIPAGARD® DMDM from Clariant Corp. This product, as supplied, is described to comprise 1,3-bis(hydroxymethyl)5,5-dimethylimidazolidine-2,4-dione, 44-46% wt. water, 17-19% wt. formaldehyde and not more than 1% of other unspecified materials. When present this may be included in effective amounts, and advantageously when present to one or more preservative compositions or preservative preparations are present in amounts of from about 0.001-1% wt. based on the weight treatment composition of which it forms a part.

Optionally the lavatory treatment compositions may comprise bleaches and/or bleach releasing compounds. Examples of such bleaches and/or bleach releasing compounds include those selected from the group of the alkali metal and alkaline earth salts of hypohalite, haloamines, haloimines, haloimides and haloamides. All of these are believed to produce hypohalous bleaching species in situ. Hypochlorite and compounds producing hypochlorite in aqueous solution are preferred, although hypobromite is also suitable. Representative hypochlorite-producing compounds include sodium, potassium, lithium and calcium hypochlorite, chlorinated trisodium phosphate dodecahydrate, potassium and sodium dichloroisocyanurate and trichlorocyanuric acid. Organic bleach sources suitable for use include heterocyclic N-bromo and N-chloro imides such as trichlorocyanuric and tribromocyanuric acid, dibromo- and dichlorocyanuric acid, and potassium and sodium salts thereof, N-brominated and N-chlorinated succinimide, malonimide, phthalimide and naphthalimide. Also suitable are hydantoins, such as dibromo- and dichloro dimethylhydantoin, chlorobromodimethyl hydantoin, N-chlorosulfamide (haloamide) and chloramine (haloamine). Particularly preferred is sodium hypochlorite having the chemical formula NaOCl Optionally an oxidizing constituent or agent may be present in the lavatory treatment compositions. Examples of such an oxidizing agent include peroxyhydrates or other agent which releases hydrogen peroxide in aqueous solution. Such materials are per se, known to the art. Peroxyhydrates are to be understood as including hydrogen peroxide as well as any material or compound which in an aqueous composition yields hydrogen peroxide. Non-limiting examples of such materials and compounds include: alkali metal peroxides including sodium peroxide and potassium peroxide, alkali perborate monohydrates, alkali metal perborate tetrahydrates, alkali metal persulfate, alkali metal percarbonates, alkali metal peroxyhydrate, alkali metal peroxydihydrates, and alkali metal carbonates especially where such alkali metals are sodium or potassium. Further useful are various peroxydihydrate, and organic peroxyhydrates such as urea peroxide. Desirably, when present, the oxidizing agent is hydrogen peroxide.

When an oxidizing agent is present, minor amounts (<1% wt.) of one or more known art hydrogen peroxide stabilizers such as one or more organic phosphonates, stannates, pyrophosphates, as well as citric acid, may also be present.

Optionally, the lavatory treatment compositions may include one or more coloring agents, which are used to impart a desirable visual appearance, e.g., color(s) to the compositions. One or more known art pigments and dyes may be advantageously included in certain embodiments and may be added in effective amounts, which, when present, are advantageously included in an amount of from about 0.00001-2% wt. Such coloring agents may be provided in an aqueous carrier, in an organic solvent carrier or a mixture thereof.

Optionally, the lavatory treatment compositions include a fragrance constituent, which may comprises one or more fragrance materials. Fragrance materials may generally be divided into three main groups: (1) the essential oils and products isolated from these oils; (2) products of animal origin; and (3) synthetic chemicals.

The essential oils consist of complex mixtures of volatile liquid and solid chemicals found in various parts of plants. Mention may be made of oils found in flowers, e.g., jasmine, rose, *mimosa*, and orange blossom; flowers and leaves, e.g., lavender and rosemary; leaves and stems, e.g., geranium, patchouli, and petitgrain; barks, e.g., cinnamon; woods, e.g., sandalwood and rosewood; roots, e.g., *angelica*; rhizomes, e.g., ginger; fruits, e.g., orange, lemon, and bergamot; seeds, e.g., aniseed and nutmeg; and resinous exudations, e.g., myrrh. These essential oils consist of a complex mixture of chemicals, the major portion thereof being terpenes, including hydrocarbons of the formula $(C_5H_8)_n$ and their oxygenated derivatives. Hydrocarbons such as these give rise to a large number of oxygenated derivatives, e.g., alcohols and their esters, aldehydes and ketones. Some of the more important of these are geraniol, citronellol and terpineol, citral and citronellal, and camphor. Other constituents include aliphatic aldehydes and also aromatic compounds including phenols such as eugenol. In some instances, specific compounds may be isolated from the essential oils, usually by distillation in a commercially pure state, for example, geraniol and citronellal from citronella oil; citral from lemon-grass oil; eugenol from clove oil; linalool from rosewood oil; and safrole from *sassafras* oil. The natural isolates may also be chemically modified as in the case of citronellal to hydroxy citronellal, citral to ionone, eugenol to vanillin, linalool to linalyl acetate, and safrol to heliotropin.

Animal products used in perfumes include musk, ambergris, civet and castoreum, and are generally provided as alcoholic tinctures.

The synthetic chemicals include not only the synthetically made, but also naturally occurring isolates mentioned above, and such may include their derivatives and compounds unknown in nature, e.g., isoamylsalicylate, amylcinnamic aldehyde, cyclamen aldehyde, heliotropin, ionone, phenylethyl alcohol, terpineol, undecalactone, and gamma nonyl lactone.

Fragrance materials as received from a supplier may be provided as an aqueous or organically solvated composition, and may include as a hydrotrope or emulsifier a surface-active agent, typically a surfactant, in minor amount, and such are frequently proprietary blends of one or more of the foregoing materials. Such fragrance materials may be suitably used as fragrance constituents.

When included in the lavatory treatment compositions, the fragrance constituent may be included in any effective amount which provides a desired olfactory benefit. Such olfactory benefit may be to impart a fragrance and benefit, to provide an odor masking benefit, or even to providing odor neutralization benefit. Advantageously, fragrance constituent comprises between about 0.01-7.5% wt. of the inventive compositions in which they form a part.

Optionally the lavatory treatment compositions may include visibly discernible materials which may, for example, be particles or particulates which are visibly discernible to a consumer, particularly by a consumer having normal "20/20" vision, visually inspecting a mass or dose of the lavatory treatment compositions applied to a hard surface. Non-limiting examples of such visibly discernible materials include materials which provide a visual effect of suspended inclusions within the mass of a lavatory treatment compositions which may be advantageous from a consumer standpoint. Such visibly discernible materials may for example be particulates of mica, colored beads such as glass beads or beads, comminuted particles or spheres formed from uncolored or colored synthetic polymers, visible light reflective particles (commonly referred to as "glitter") which are typically formed of comminuted metallized or reflective polymer particles, alginate beads such as those described in PCT/US95/08313, U.S. Pat. No. 7,196,046, U.S. Pat. No. 7,291,586 B2, as well as other visibly discernible materials known to the art which would provide a similar function. Preferably such visibly discernible materials have a maximum dimension in the range of from about 100 to about 1000 µm.

Optionally the lavatory treatment compositions may include one or more inert inorganic or inert organic fillers compounds or materials which are preferably insoluble in water or in organic solvents. Non-limiting examples of such inert fillers include powders such as silicates, chalk, talc, kaolin, chemically modified magnesium aluminum silicate, hydrated aluminum silicate, fumed silica, and mixtures thereof Optionally the lavatory treatment compositions may include one or more constituents which function as viscosity modifying agents or thickeners. Non-limiting examples of such materials include polysaccharide polymers especially those selected from cellulose, alkyl celluloses, alkoxy celluloses, hydroxy alkyl celluloses, alkyl hydroxy alkyl celluloses, carboxy alkyl celluloses, carboxy alkyl hydroxy alkyl celluloses, naturally occurring polysaccharide polymers such as xanthan gum, guar gum, locust bean gum, tragacanth gum, or derivatives thereof Further constituents which function as viscosity modifying agents or thickeners include polycarboxylate polymers, polyacrylamides, clays, and mixtures thereof.

Non-limiting examples of useful cellulose derivatives include methyl cellulose ethyl cellulose, hydroxymethyl cellulose hydroxy ethyl cellulose, hydroxy propyl cellulose, carboxy methyl cellulose, carboxy methyl hydroxyethyl cellulose, hydroxypropyl cellulose, hydroxy propyl methyl cellulose, ethylhydroxymethyl cellulose and ethyl hydroxy ethyl cellulose.

Non-limiting examples of useful polycarboxylate polymers are those have a molecular weight from about 500,000 to about 4,000,000, preferably from about 1,000,000 to about 4,000,000, with, preferably, from about 0.5% to about 4% crosslinking Preferred polycarboxylate polymers include polyacrylate polymers including those sold under trade names Carbopol®, Acrysol® ICS-1 and Sokalan®. The preferred polymers are polyacrylates. Other monomers besides acrylic acid can be used to form these polymers including such monomers as ethylene and propylene which act as diluents, and maleic anhydride which acts as a source of additional carboxylic groups.

Non-limiting examples of further useful polycarboxylic acid polymer compositions which can be employed include, for example, crosslinked copolymers of acrylates, (meth) acrylic acid, maleic anhydride, and various combinations thereof.

Non-limiting examples of useful clay thickeners include colloid-forming clays, for example, such as smectite and/or attapulgite types. The clay materials can be described as expandable layered clays, i.e., aluminosilicates and magnesium silicates. The term "expandable" as used to describe the instant clays relates to the ability of the layered clay structure to be swollen, or expanded, on contact with water. The expandable clays used herein are those materials classified geologically as smectites (or montmorillonite) and attapulgites (or polygorskites). Commercially available clays include, for example, montmorillonite, bentonite, volchonskoite, nontronite, beidellite, hectorite, saponite, sauconite and vermiculite. The clays herein are available under various trade names such as Gelwhite GP, Gelwhite H, Mineral Colloid BP, and Laponite from Southern Clay Products, Inc., Texas; and Van Gel O from R. T. Vanderbilt.

Further constituents which may be optionally included in the lavatory treatment composition include one or more of: inorganic filler materials, such as one or more of silica, fumed silica, silica dioxide, carbon black, comminuted polymer beads or particulates, sodium silicate. Further materials based on rosins, tall oil and/or terpene compounds may also be included, e.g., polyterpenic resins (e.g., Dercolyte LTG, ex. DRT), or rosin esters, such as diethylene glycol rosin esters (e.g., Dertoline DEG 2, ex. DRT); certain of such may be useful in the organic solvent constituent. Exemplary chelating agents include alkali metal, ammonium and substituted ammonium polyacetates, carboxylates, polycarboxylates and polyhydroxysulfonates, as well as tetra sodium salt of glutamic acid-N,N-diacetic acid, as well as methyl-glycine-diacetic acid. Nonlimiting examples of commercially available chelating agents include those marketed under the "Dissolvine" trademark (ex. AkzoNobel) including Dissolvine GL-PD-S, and Dissolvine E-CA-10 materials. Further useful as an optional constituent are butane homopolymers, e.g., polyisobutene, such as may be commercially obtained as TPC 1350 from Texas Petro Chemicals Co. Further useful as an optional constituent is an emulsifying agent, preferably sucrose acetate isobutyrate such as is commercially available as Eastman SAIB-100 (ex. Eastman Chemical Co.)

Other optional constituents, although not specifically elucidated above, may also be considered useful for inclusion in the lavatory treatment compositions particularly wherein such impart a further aesthetic or technical benefit to the said lavatory treatment compositions.

The lavatory treatment compositions used in the lavatory treatment devices of the invention may be formed combining the constituents, and mixing them in a suitable vessel, for example a laboratory beaker to which is provided a stirrer, preferably a propeller or paddle type store mounted on a shaft driven by an electric motor, and preferably also wherein the laboratory beaker is mounted upon a hotplate or other heating source in order to allow variation in the control of the temperature between about room temperature (approx. 20° C.) and about 100° C. Such temperature control facilitates the formation of the compositions wherein one or more the constituents may have a melting point above room temperature. Advantageously the compositions of invention are formed by first producing a first pre-mixture is formed by blending the adhesion promoter based on a fatty alcohol polyglycol ether, the organic solvent constituent, the at least one detersive surfactant, and when present any co-adhesion promoter constituents. Such blending may be achieved by suitably mixing the foregoing constituents at a suitable temperature within the foregoing range (20° C.-100° C.) for sufficient time in order to ensure that a homogenous mixture is formed. Typically, depending upon the volume of the mixing vessel and the characteristics of the stirrer a homogenous mixture is formed, suitably such occurs between 5 min.-120 min. of stirring. If necessary, the composition may be allowed to cool (if it was raised to an elevated temperature) in order to allow for the introduction of further constituents, e.g., one or more optional constituents such as fragrances, colorants, etc., which are preferably added to the homogenous mixture, at a temperature suitable for their addition. For example, where fragrances are used, advantageously the temperature of the homogenous mixture is sufficiently low to avoid the premature flashing off of one or more the fragrance compounds prior to being blended. Advantageously, such further constituents are first formed into a second pre-mixture in a separate vessel, with a separate stirrer, at a suitable temperature, e.g. room temperature (approx. 20° C.) and about 100° C. as stirring continues, typically for between 5-120 min. until the second pre-mixture is homogenous. Thereafter, measured amounts of the second pre-mixture may be added, under stirring conditions, to the first pre-mixture as suitable temperature in order to form a homogenous blend from the first, and second pre-mixtures. Subsequently a measured amount of water, which may optionally include any further remaining constituents not already provided in the first premixture and/or the second premixture, which water is preferably at a temperature of between about 10-50° C., is added to this resultant homogenous blend. It is been observed that that upon addition of the water, even under reduced stirring conditions that the onset of the formation of the gel is swift and with some formulations nearly instantaneous, sometimes forming on the order of between 0.1-15 seconds, preferably between about 0.5-10 seconds as the water (with any remaining constituents) is combined to the balance of the constituents of the homogenous mixture formed from the first and second pre-mixtures. Advantageously, the resultant gel is allowed to rest in undisturbed state for a number of hours thereafter, preferably for least about 24 hours to allow for the "setting" of the resultant gel.

The addition of the water to the balance of the constituents of the homogenous mixture may take place in a suitable container. For example, the water may be added to the beaker containing the quantity of the homogenous mixture but advantageously, in certain embodiments, an aliquot of the homogenous mixtures provided either concurrently, or serially with a measured aliquots of water directly into a cavity which forms part of a lavatory treatment device, such as is hereafter described or referred to in one or more of the drawing figures. Alternately the addition of the water to the balance of the constituents of the homogenous mixture may take place in a container or mold which contains part of a lavatory treatment device such that after the lavatory treatment composition is sufficiently rigid, it is removable from the container or mold along with the part of the lavatory treatment device. Such allows for simplified processes for the manufacture of lavatory treatment devices according to one or more aspects of the invention.

Following their production, preferred lavatory treatment compositions of the invention are viscous or pasty, and may be characterized in having a viscosity in the range of from about 150,000 cP to about 7,000,000 cP, but preferably from about 200,000 to about 5,000,000. The viscosity may be determined utilizing conventional analytical instruments. In certain preferred embodiments the lavatory treatment compositions are translucent or transparent, and may optionally be colored. In particularly preferred embodiments the lavatory treatment compositions of the lavatory treatment devices are essentially transparent ringing gels, which are also optionally but preferably colored and fragranced, so to provide an attractive aesthetic presentation to a consumer or user of the lavatory treatment device.

Although, in certain preferred embodiments the lavatory treatment composition may exhibit a characteristic, which might render them adapted to be used by directly applying them to hard surfaces, which may be vertical, or sloped, where they may be applied and retained, according to the present invention the lavatory treatment compositions are no so used but rather are provided as part of a lavatory treatment device, which positions the lavatory treatment composition within a part of a lavatory appliance such that, at least upon initial installation, the lavatory treatment composition is spaced away from any of the surfaces of the of lavatory treatment device so that they do not adhere to such surfaces. Rather, in preferred embodiments the lavatory treatment compositions form part of an ITB lavatory treatment device or an ITC lavatory treatment device which is subsequently installed at a suitable location within a lavatory appliance, preferably a toilet bowl. Preferably the configuration of the lavatory treatment composition and the lavatory treatment device is such that the lavatory treatment composition is physically separated from (isolated from) any surface of the lavatory appliance so that its form as a gel, it does not come into direct physical contact with said surface, but its constituents only come into contact with the lavatory appliance after it has been first contacted with water, e.g., flush water, into which it may be eluted to form a lavatory treatment liquid which comes into contact with the lavatory appliance. Preferably such a condition of physical separation between the lavatory treatment composition and any surface of the lavatory appliance occurs at least at the time of the initial installation of the lavatory treatment device, but more preferably the said condition of physical separation persists through at least the initial 25%, more preferably at least the initial 50%, still more preferably at least the initial 75% of the service life of the lavatory dispensing device. In the most preferred embodiments, physical separation between the lavatory treatment composition and any surface of the lavatory appliance is maintained throughout the entire service life of the lavatory treatment device.

Following installation of the lavatory treatment device, the lavatory treatment compositions may be flushed away after a plurality of flushing operations, preferably following a relatively large number of flushing operations. This is facilitated as at least a part of the surface of the lavatory treatment compositions are exposed to impingement by water, present within the lavatory appliance. Such water may be the water stored in the cistern, when the lavatory treatment device is used as an ITC device, or may be flush water released into the toilet bowl when the lavatory treatment device is used as an ITB device. Contact of the water with the lavatory treatment composition causes its erosion or dissolution and forms the lavatory treatment liquid used to treat the lavatory appliance.

While it is naturally understood that the operating parameters of lavatory devices, e.g., toilets, vary considerably and that the range of lavatory treatment compositions which are taught herein are also variable, preferably, they comprise a mass of at least about 1 gram, to about 200 grams, but preferably the lavatory treatment compositions are present in the lavatory treatment devices in amounts of from about 3 to about 100 grams, yet more preferably from about 25 to about 45 grams. While the entire mass or quantity of the lavatory treatment composition may be present in a single discrete body or block of material, such is not an essential feature and the mass of the lavatory treatment composition may be divided into two or more separate or separable bodies or blocks which may be present in one or more parts of the lavatory treatment device.

Preferably, the mass of the lavatory treatment composition is present in a sufficient amount in the lavatory treatment device such at in normal domestic use as an ITB device in a domestic toilet bowl, the device has a useful service life. Preferably the lavatory treatment device operates to provide a satisfactory level of delivery of the lavatory treatment liquid or at least 5, and in order of increasing preference, for at least 10, 15, 20, 25, 30, 35, 40, 45, 50, 55, 60, 65, 70, 75 and 80 flushes, or until the lavatory treatment composition is fully diluted or eroded by the flushing water from the remaining part(s) of the lavatory treatment device.

The lavatory treatment devices of the invention comprising the lavatory treatment compositions taught herein are particularly well adapted for use with a lavatory appliance in order to provide a cleaning and/or fragrancing and/or sanitizing and/or other technical benefit thereto. In use, the lavatory treatment device is mounted within or upon a part of the lavatory appliance such that the lavatory treatment composition is exposed to and contacted with water present in the lavatory appliance. For example when the lavatory treatment device is an ITB device, it may be provided to the interior of a toilet bowl so that the lavatory treatment composition is placed in the path of flush water when the lavatory appliance is flushed. For example, where the ITB device is used in a toilet bowl or bidet, the device may be suspended from a part of a rim of the bowl of such devices. When the ITB device is used in a urinal, the device containing the lavatory treatment composition may be placed into the urinal itself such as near its drain without being suspended from any part of the urinal. Where the lavatory treatment device is an ITC device, it may be placed within any part of the cistern or supply tank of a toilet bowl wherein the lavatory treatment composition may be either fully continuously immersed (e.g., by placement of the ITC device at the base of the cistern), be fully intermittently immersed (e.g., by placement of the ITC below the upper surface of the water of a cistern when such is prior to a flush operation, but where the ITC is above the upper surface of the water of a cistern the conclusion of a flush, but prior to refilling of the cistern) or be intermittently partially immersed (e.g., by placement of the ITC only partially below the upper surface of the water of a cistern when such is prior to a flush operation, but where the ITC is above the upper surface of the water of a cistern the conclusion of a flush, but prior to refilling of the cistern). In either mode of operation and/or configuration, water comes into contact with the lavatory treatment composition forming part or the lavatory treatment device. Again, the water contacting or impinging the lavatory treatment composition dissolves or erodes some of the said composition, and thus forms the lavatory treatment liquid. Depending upon the specific constituents used to form the lavatory treatment compositions, various technical benefits may be provided by the thus formed lavatory treatment liquid.

Thus, an aspect of the invention provides a method of for treating a lavatory appliance comprising the steps of: providing a lavatory treatment device comprising a lavatory treatment composition as described herein to a lavatory applicant, and at least periodically forming a lavatory treatment liquid within the lavatory appliance which is used to treat one or more surfaces of the lavatory appliance, e.g, the bowl of a toilet or bidet, or the interior surface of a urinal.

Various configurations of the lavatory treatment device, including certain particularly preferred embodiments, are depicted on the following figures. In the accompanying figures, like elements are indicated using the same numerals throughout the figures.

FIG. 1 depicts a hanger 10 comprising a hook end 20 comprising an end member 12 flexibly attached to a top member 14 as well as part of the stalk 16. For sake of convenient illustration, the hanger 10 is illustrated without the body 50 of the lavatory treatment composition encasing part of the hanger (as is depicted on later figures, e.g. FIGS. 10A, 10B) although it is to be understood that such is necessarily present, and that the body 50 is affixed to, or encases or enrobes at least a part of the hanger, preferably at least the plate 30. Depending from the end of the stalk 16 distally from the hook end 20 is a plate 30. As can be seen from the perspective view provided by FIG. 1, the plate itself is generally rectangular in configuration, and it is coplanar with the ribbon-type or strip-type configuration and construction of both the stalk 16 and hook end 20. The plate 30 has a width dimension "W1" as well as a height dimension "H1" and as depicted, desirably the width is greater than the height. As is visible from the figure, the hanger 10 is generally symmetrical about a center line "CL" which is drawn with respect to the midline of the stalk 16. The center line does not exist as an actual element of the device but is illustrated for the sake of convenient reference. While not illustrated with sufficient particularity in the figure, it is of course understood that the plate, stalk 16 and the hook end 20 all have a thickness which may be consistent throughout, or which can vary.

Figure 2:
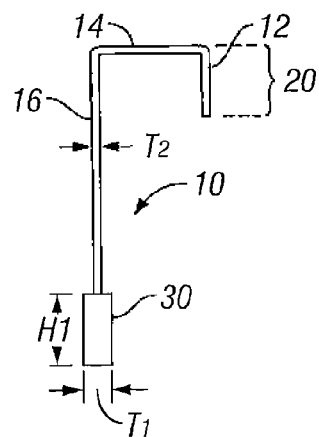

FIG. 2 depicts a side view of a further embodiment of the hanger 10 of FIG. 1. Again, for sake of convenient reference, the body 50 of the lavatory treatment composition encasing part of the hanger has been omitted, but is necessarily present as described with reference to FIG. 1. As is more clearly seen in this figure, the hook end 20 is formed from first and second elements 12, 14 and part of the stalk 16. Depending from the stalk 16 is the plate 30. In this embodiment the plate 30 has a thickness "T1" which is greater than the thickness "T2" of the stalk 16 and the hook end 20. Of course, it will be understood that each of the hook end, stalk, and plate can have different thicknesses or can all share the same thickness as illustrated in FIG. 1.

Figure 3:
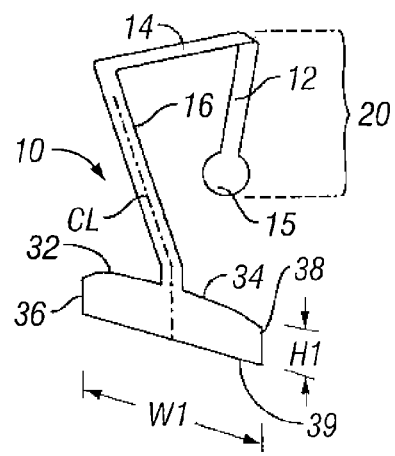

FIG. 3 depicts a further embodiment of a hanger 10 according to the invention, in which the hook end 20 is a flexible element. Again, for sake of convenient reference, the body 50 of the lavatory treatment composition encasing part of the hanger has been omitted, but is necessarily present as described with reference to FIG. 1. As can be seen from the figure, the hook end is comprised of a hook end element 12 flexibly connected to a top element 14 which in turn is flexibly connected to the stalk 16. At the end opposite the hook end, depends the plate 30. With regard to the hook end, as can be seen, at the terminal end of the hook end element 12 is seen a broadened region which is referred to as a "pad" 15. The pad region is of the same thickness as the first element 12, but is slightly broader. The width of the pad end 15 is greater than the width of the first element 12. This increased width is sometimes useful to stabilize the hook end of the lavatory treatment device when suspended upon part of a sanitary appliance. As is further visible from FIG. 3, the plate 30 is substantially planar in configuration has a width W1 as well as height H1 and is symmetric around the center line CL of the stalk 16. The plate has a generally linear bottom edge 39 at opposite ends thereof to generally straight end walls 36, 38 which end walls proceed and extend to the stalk 16 via sloping top walls 32, 34.

Figure 4:
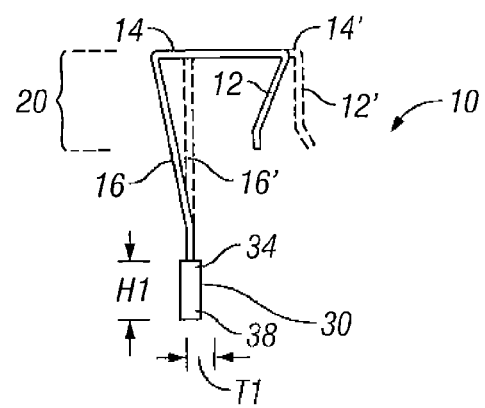

FIG. 4 depicts the hanger 10 of FIG. 3 in both a "folded" as well as in an "unfolded" configuration. Again, for sake of convenient reference, the body 50 of the lavatory treatment composition encasing part of the hanger has been omitted, but is necessarily present as described with reference to FIG. 1. As seen from the solid line elements depicted on FIG. 4, the hanger 10 on the folded configuration illustrates, that when the hook end and the stalk are untensioned, the hook end 20 is retained in a closed configuration. In the unfolded configuration, as depicted by the elements depicted in a broken line format, the first element 12' and the pad 15' are extended away from the stalk 16 and are more distantly positioned with respect to the stalk than in the prior, folded configuration. Typically, this also causes a degree of translation of the top element 14' which may extend down to, include a portion of the stalk 16' as well. When made of a flexible material, in the unfolded configuration as depicted in FIG. 4, the elastic bias of the material of construction, such as a polymer, tends to cause the hook end to seek to return to the folded configuration. However, when placed about the rim of a portion of a sanitary device, i.e. a toilet bowl, this action causes the hook end to impart a degree of gripping to that portion of the rim upon which it is mounted. This is turn helps retain the relative position of the hook end, as well as that of the lavatory treatment device until repositioned, or removed by a consumer.

FIG. 5 depicts a still further embodiment of a hanger 10. In this embodiment, the hanger includes a coiled hook end 20 comprised of the first element 12, the second element 13 and a top element 14 which is in a compressed, coiled arrangement thus making it particularly convenient to include in a consumer package. Again, for sake of convenient reference, the body 50 of the lavatory treatment composition encasing part of the hanger has been omitted, but is necessarily present as described with reference to FIG. 1. The top end of the top element 14 extends to a stalk 16 having at its opposite end a depending plate 30. In this configuration, the plate 30 is oblate in shape and is generally symmetrical about a center line (CL). The plate has a width dimension (W1) as well as a height dimension (H1). Further, the plate illustrates that it can be produced with perforations passing there through. Here, two similarly shaped, generally triangular passages 33, 33' are provided. As has been discussed previously in the specification, while it is contemplated that the plate of the hanger may include one or more perforations passing there through, for reasons observed although not yet fully understood by the applicants, it is believed that the use of plates having such perforations passing there through are to be preferably avoided as such may undesirably reduce the service life of the lavatory treatment device.

FIG. 6A depicts a still further embodiment of a hanger 10 according to the invention. As is shown, the hanger includes a hook end which is comprised of the first element 12, flexibly connected to a second element 13, which is in turn flexibly connected to a top element 14, which in turn is flexibly connected to a part of the stalk 16. The opposite end of the stalk terminates in a generally oblate shaped plate 30 having a width dimension (W1), a height dimension (H1) wherein the plate is generally symmetrically about the center line (CL) as depicted in the dotted line drawn on FIG. 6. Whereas the hanger is depicted in a folded or otherwise coiled configuration, it is to be understood that the hook end can be extended by a user of the hanger and the lavatory treatment device to reconfigure said hook end 20 to form a hook end which can be used to suspend the hanger and the lavatory treatment device upon a part of a sanitary device particularly a toilet bowl rim. The embodiment according to FIG. 6A also illustrates that, according to preferred embodiments, the plate 30 is substantially planar and as is shown in FIG. 6A, it is of generally uniform thickness. The embodiment depicted in FIG. 6A is preferred in that the hook end is particularly well coiled when in its folded configuration, but when uncoiled or in its unfolded configuration, provides a significant degree of tension which is useful in retaining the respective position of the lavatory treatment device when installed upon a sanitary appliance, particularly when the hook is affixed on a part of a toilet bowl rim. Furthermore, FIG. 6 depicts that that embodiment also includes a slanting neck 17 formed as part of the stalk 16 and immediately adjacent to the region of the plate 30 which is connected to the stalk 16. As depicted, the neck positions the plate at a position which is beneath the major portion of the stalk 16 but is parallel thereto. This positioning beneath the major part of the stalk 16 is beneficial and ultimately, it acts to also thereby position the body 50 of a lavatory treatment composition enrobing the plate 30 such that when mounted upon a toilet bowl, the body of the lavatory treatment composition is in contact with, or is in very proximity to the interior sloping side wall of a toilet bowl. Such positioning is advantageous in that it ensures that the said body remains in the flow path of the flush water throughout the useful service life of lavatory treatment device.

FIG. 6B depicts a lavatory treatment device 80 according to the invention wherein the hook 10 according to FIG. 6A includes a body 50 of the lavatory treatment composition which encases the plate 30.

Figure 7A:
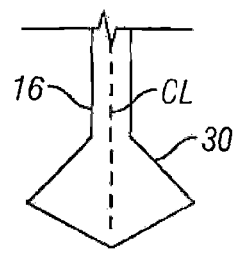
Figure 7B:
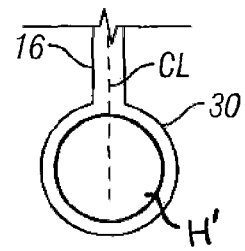
Figure 7C:
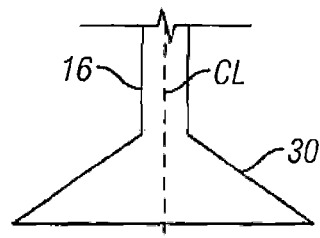
Figure 7D:
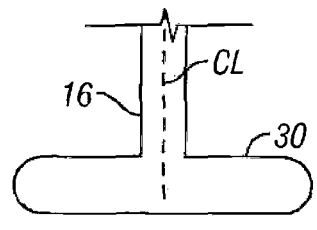

FIGS. 7A through 7D depict various alternate configurations which may also be used for the plate 30 for the hanger 10 as described herein. FIG. 7A depicts a diamond-shaped plate 30 depending at one vertex from the stalk 16. FIG. 7B depicts a substantially circular plate 30 depending from one part of its circumference from the stalk 16, and having a central hole "H'" (or perforation H') passing therethrough thus providing a substantially ring shaped plate 30. FIG. 7C depicts an equilateral-triangular shaped plate 30 depending at one vertex from the stalk 16. FIG. 7D depicts a further plate 30 which is generally rectangular but having two opposite semi-circular ends depending from the stalk 16. In each of the foregoing, it is seen that the configuration of the plates is generally symmetrical about the center line, CL.

Figure 8:
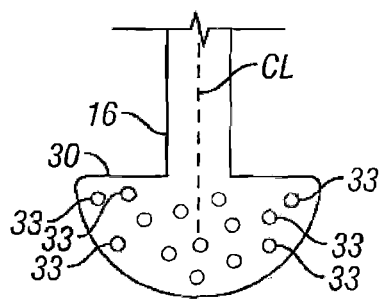

FIG. 8 depicts an embodiment of a portion of the hanger wherein the plate 30 includes a series of perforations 33 passing there through. As is depicted, the perforations are not symmetrical with respect to either the center line CL or the configuration of the semi-circular shaped plate 30. As noted above, plates 30 having perforations passing there through are less preferred embodiments of the hangers and useful with the lavatory treatment devices taught herein.

Figure 9B:
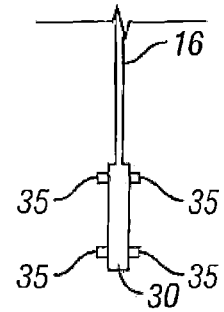
Figure 9A:
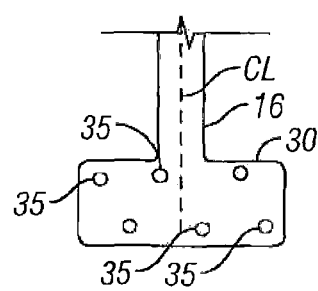

FIGS. 9A and 9B depict in two views an embodiment of a plate 30 depending from a stalk 16 wherein the plate comprises at least one, here a plurality of projections 35 extending outwardly from the generally planar and opposite faces 37, 37' of the plate. As is seen in particular in FIG. 9B, the projections 35 are in the form of generally cylindrical studs having a base coincident with the respective face 37, 37' of the plate 30. The studs terminate at flat ends. The studs have a height which is approximately equal to, or slightly greater than thickness of the plate 30. Again, while these figures depict the utility of outwardly extending elements extending outward from the plate, again, as noted above embodiments of the hanger having such outwardly extending elements from the plate are less preferred.

Figure 10A:
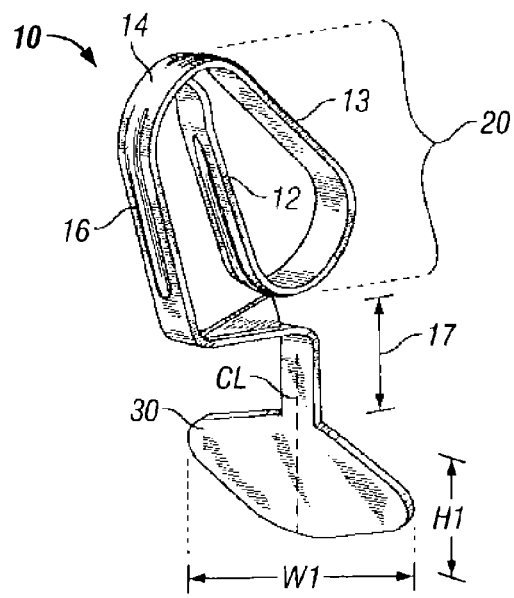
Figure 10B:
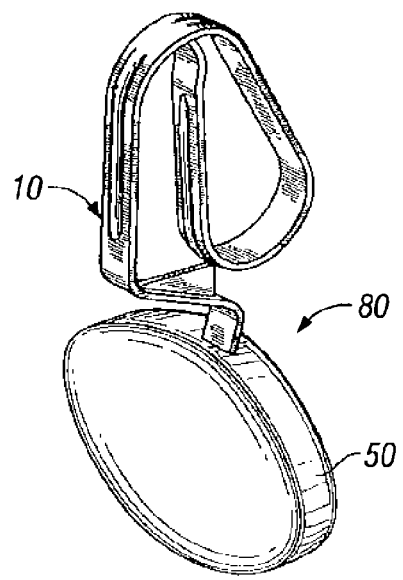

FIGS. 10A and 10B depict a still further embodiment of a hanger 10 according to the invention; in FIG. 10A depicts the hanger 10 without the body 50 of the lavatory treatment composition, whereas FIG. 10B depicts the lavatory treatment device 80 which includes the hanger 10 having affixed thereto a body 50 encasing part of the hanger. As is shown, the hanger includes a hook end 20 which is comprised of the end member 12, flexibly connected to element 13, which is in turn flexibly connected to a top element 14, which in turn is flexibly connected to a part of the stalk 16. The stalk extends downwardly through a neck section 17, and terminates at a generally oblate shaped plate 30 having a width dimension (W1), a height dimension (H1) wherein the plate is generally symmetrically about the center line (CL) as depicted in the dotted line drawn on the figure. The illustrated embodiment includes a bent neck 17 which is angled, thereby configuring the major part of the stalk 16 to be non-parallel to the plane of the plate 30, but rather is angled with respect thereto. Whereas the hanger 20 is depicted in a folded or otherwise coiled configuration, it is to be understood that the hook end can be extended by a user of the hanger and the lavatory treatment device to reconfigure said hook end 20 to form a hook end which can be used to suspend the hanger and the lavatory treatment device upon a part of a sanitary device particularly a toilet bowl rim. FIG. 10A illustrates that, according to preferred embodiments, the plate 30 is substantially planar and as is shown is of a generally uniform thickness. The embodiment depicted in FIGS. 10A and 10B, it is preferred in that the hook end 20 is tightly coiled when in its folded configuration, which make it convenient to package prior to its deployment and use, but when uncoiled or in its unfolded configuration and suspended from a part of a lavatory appliance, provides a significant degree of tension which is useful in retaining the respective position of the lavatory treatment device when installed upon a sanitary appliance, particularly when the hook is affixed on a part of a toilet bowl rim. Furthermore, as seen the bent neck 17 positions the plate 30 at a position which is rearward of the major portion of the stalk 16 but retains the plate 30 as being generally parallel thereto. Such positioning of the plate 30 upon which is present a body of the lavatory treatment composition rearward of the major part of the stalk 16 is beneficial as ultimately, it acts to also thereby position the body enrobing the plate 30 such that when mounted upon a toilet bowl, the body of the lavatory treatment composition is within the interior of the toile bowl, but spaced away from the sloping side wall of the toilet bowl. Such positioning is advantageous in that it ensures that the body remains in the flow path of the flush water throughout the useful service life of the lavatory dispensing device, but preferably the body does not come into contact with the side wall of the toilet bowl. As is understood from comparing the depiction of FIG. 10A with FIG. 10B, the body 50 of the lavatory treatment composition fully encases the plate 30 and part of the bent neck 17 of the hanger.

Figure 11A:
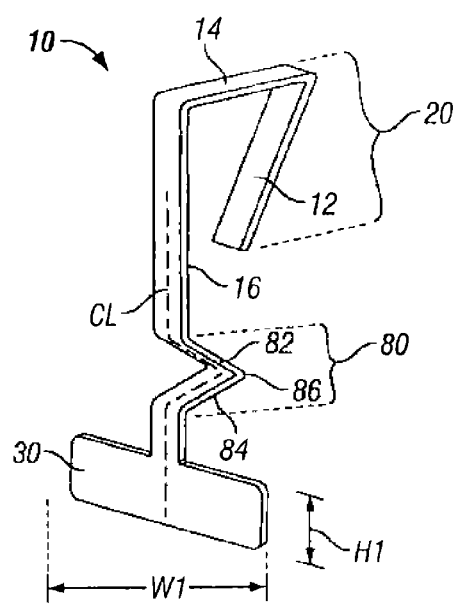
Figure 11B:
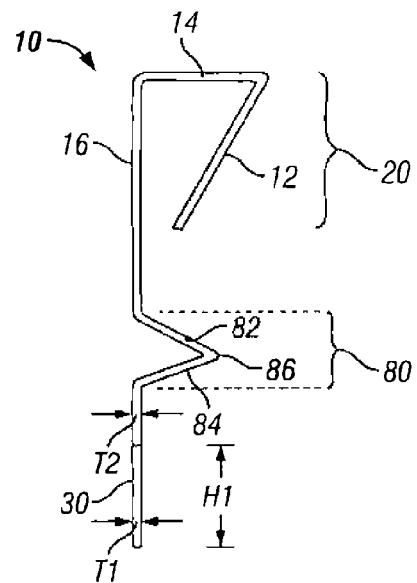

FIGS. 11A and 11B depict a hanger 10 comprising a hook end 20 comprising an end member 12 flexibly attached to a top member 14 as well as part of the stalk 16. Depending from the end of the stalk 16 distally from the hook end 20 is a plate 30. Again, for sake of convenient reference, the body 50 of the lavatory treatment composition encasing part of the hanger has been omitted, but is necessarily present as described with reference to FIG. 1. As can be seen from the perspective view provided by FIG. 11A, the plate itself is generally planar and rectangular in configuration, and it is coplanar with the configuration and construction of both the stalk 16 and hook end 20. The plate 30 has a width dimension "W1" as well as a height dimension "H1" and as depicted, desirably the width is greater than the height. As is visible from the figure, the hanger 10 is generally symmetrical about a center line "CL" which is drawn with respect to the midline of the stalk 16. The center line does not exist as an actual element of the device but is illustrated for the sake of convenient reference. As is also visible in the figures, a portion of the stalk 16 is configured to extend rearwardly, namely in the direction of the hook end 20 to form a peak section 80. In the embodiment depicted, the peak section comprises a first peak segment 82 which extends rearwardly from the stalk 16 to a peak 86, and a second peak segment 84 which extends rearwardly from the stalk 16 to the same peak 86. As is visible in the depicted embodiment of FIG. 1. the stalk 16, first peak segment 82, peak 86, second peak segment 84 and the plate 30 are all integrally formed as parts of the hanger 10, and the first peak segment 82, peak 86, second peak segment 84 together define a peak section 80, which is preferably distal from the hook end 12 and nearer to, or adjacent to the plate 30. This is not required, but is preferred in certain embodiments as such requires no assembly subsequent to the initial fabrication of the hanger 10. As is also visible, the peak section 80 is a conveniently formed by the shape of the hanger which is formed by bends or other junctures between the respective segments and between the respective segments and the stalk 16 or plate 30. In the embodiment shown, the length of the first peak segment 82 and the second peak segment 84 are of equal lengths, however this is nor required of hangers 10 of the present invention. While not illustrated with sufficient particularity in the figure, it is of course understood that the plate, stalk 16 and the hook end 20 all have a thickness which may be consistent throughout, or which can vary. As is more clearly seen in FIG. 11B, the hook end 20 is formed from first and second elements 12, 14 and part of the stalk 16. In the embodiment shown, the length of the first peak segment 82 and the second peak segment 84 of the peak section 80 are of the same length, with both the first peak segment 82 and the second peak segment 84 joining at the peak 86. Depending from the stalk 16 is the plate 30. In this embodiment the plate 30 has a thickness "T1" which is equivalent to the thickness "T2" of the stalk 16 and the hook end 20. Of course, it will be understood that each of the hook end, stalk, and plate can have different thicknesses or can all share the same thickness as illustrated in FIG. 11A.

An important feature of the embodiment according to FIGS. 11A and 11B is that the peak section 80 operates as a standoff element. Most preferably the dimensions of the peak section 80 are such that, when a body of a lavatory treatment composition 50 is present on the hanger 10, preferably affixed to a part of the plate 30, e.g. such as being adhered to a face thereof opposite to that of the peak section 80, or at least partially encasing the plate 30, the dimensions are such that when the lavatory dispensing device is mounted on or in a lavatory appliance the body of the lavatory treatment composition is physically spaced away from any direct physical contact with the lavatory appliance, e.g., a sidewall thereof due to the peak section 80 whose peak 86 may be in direct contact with a part of the lavatory appliance, e.g., a sidewall thereof.

Figure 12A:
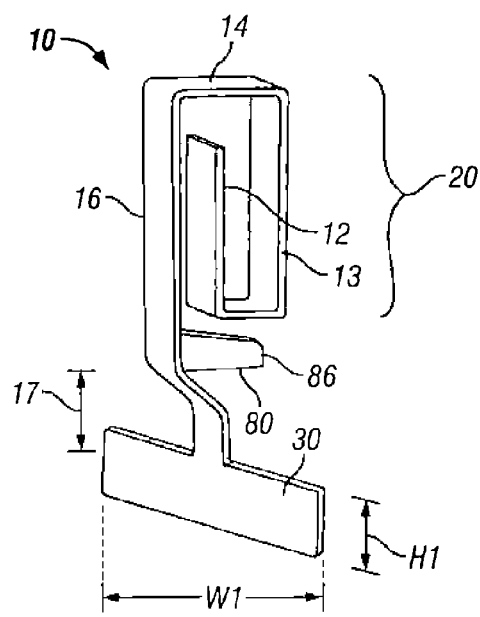
Figure 12B:
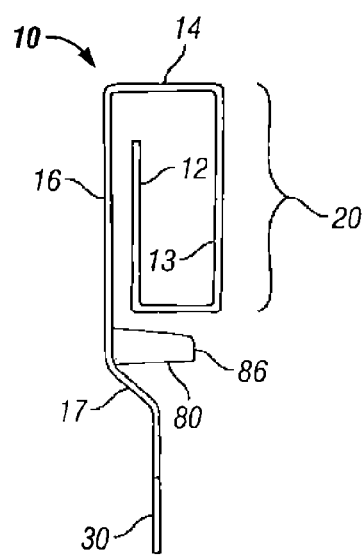

FIGS. 12A and 12B depict a further embodiment of a hanger 10 according to the invention, in which the hook end 20 is a flexible element, and a standoff element 80 which is intermediate the hook end and the plate 30 of the hanger. Again, for sake of convenient reference, the body 50 of the lavatory treatment composition encasing part of the hanger has been omitted, but is necessarily present as described with reference to FIG. 1. The standoff element 80 extends rearwardly from a part of the stalk 16 in the same direction as the hook end 20 extends from the stalk 16. While the hook end is integrally formed with stalk 16 and is proximate to the plate 30 as is illustrated in the figures, it is to be understood that the standoff element 80 may be a discrete element which may be affixed to a part of the hanger 10, advantageously to a part of the stalk 16 by any suitable means. Inter alia, such means may be mechanical means such as interlocking elements such as cooperating snap-fittings and/or chemical means such as an adhesive or by welding or fusing of these elements. As can be seen from the figures, the hook end is comprised of a hook end element 12 flexibly connected to second hook element 13 which is in turn connected to a top element 14 which in turn is flexibly connected to the stalk 16. At the end of the stalk 16 opposite the hook end, viz, the distal end of the stalk depends the plate 30, here having an planar, oblate configuration. As is further visible from FIG. 12A, the plate 30 is substantially planar in configuration has a width W1 as well as height H1 and is symmetric around the center line CL of the stalk 16. The plate 30 has a generally rectangular configuration and depends from the stalk 16 via an intermediate bent neck section 17 of the stalk 16.

While not specifically illustrated in FIGS. 12A and 12B it is to be understood that the hook end 20 of the hanger 10 is depicted in a first, "folded" configuration which permits for the hanger 10 to be compact and conveniently packaged. However, when at least the hook end 20 of the hanger 10 is fabricated of a flexible material, the elements of the hook end 20, especially the hook end element 12 flexibly connected to second hook element 13 may be flexed to form the hook end 20 so that it may be placed about the rim of a portion of a sanitary device, i.e. a toilet bowl. Such elements form an articulated hook which may be extended from the stalk 16. This action imparts tension to the hook end 20 and also causes the hook end to 20 impart a degree of gripping to that portion of the rim upon which it is mounted. This is turn helps retain the relative position of the hook end, as well as that of the cageless lavatory device until repositioned, or removed by a consumer. At the same time however the peak point 86 of the standoff element 80 is adapted to contact a part of the sanitary appliance, typically a sidewall of a toilet bowl, and to concurrently also ensure that when the lavatory dispending device is mounted on or in a lavatory appliance the body of the lavatory treatment composition present is physically spaced away from any direct physical contact with the lavatory appliance, e.g., a sidewall thereof.

Figure 13A:
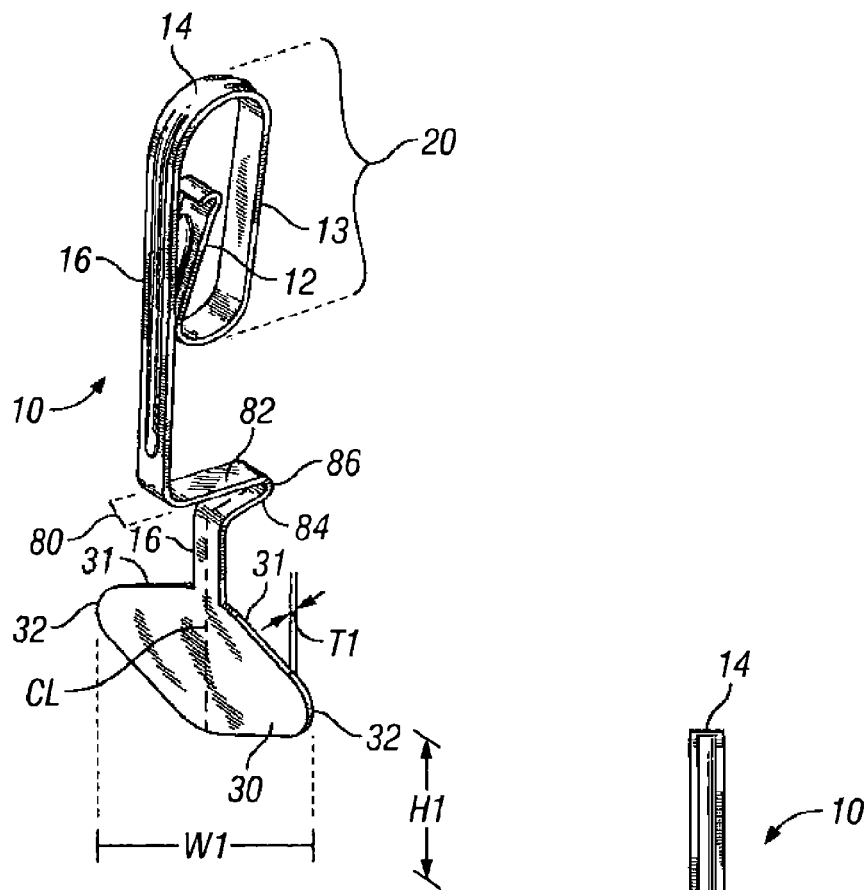
Figure 13B:
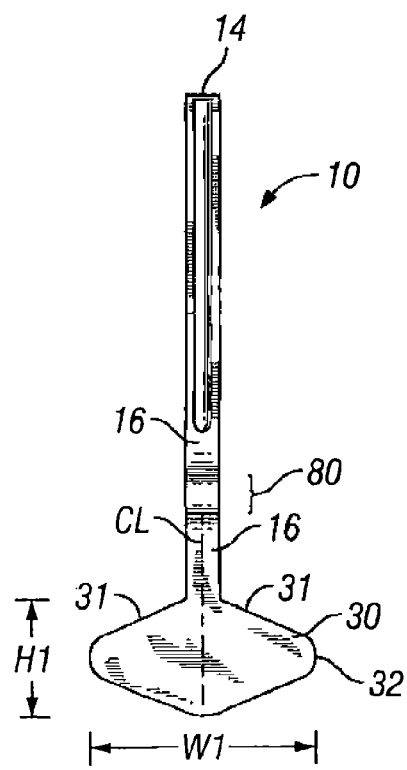
Figure 13C:
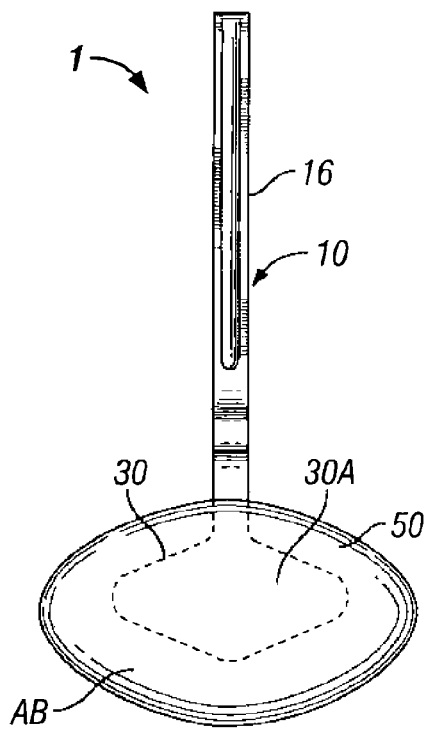
Figure 13D:
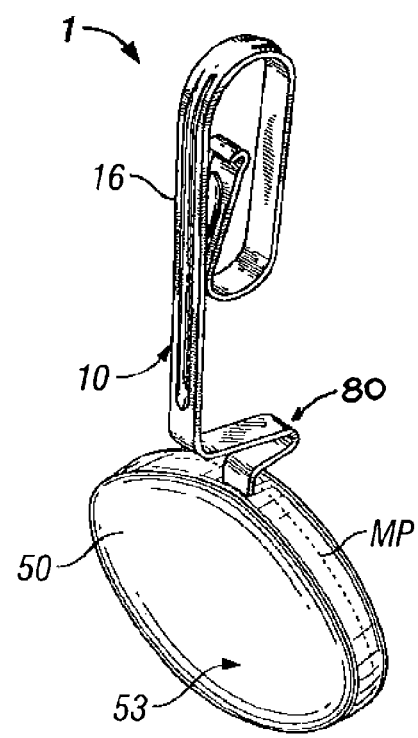

FIGS. 13A, 13B, 13C and 13D depict in various views of a preferred embodiment of a hanger 10 according to the invention which comprises a peak section 80, and which is illustrated both with and without a body 50 of the lavatory treatment composition affixed to the plate 50. In these figures, the one-piece hanger 10 formed of a flexible material, e.g., a thermoplastic polymer. The hanger 10 comprises a hook end 20 comprising a first hook element 12, a second hook element 13 and a top member 14 which in turn is connected to a downwardly extending stalk 16, which terminates in plate 30. Intermediate the hook end 20 and the plate 30, a portion of the stalk 16 is configured to extend rearwardly, namely in the direction of the hook end 20 to form a peak section 80. As depicted, the peak section 80 comprises a first peak segment 82 which extends rearwardly from the stalk 16 to a peak 86, and a second peak segment 84 which extends rearwardly from the stalk 16 to the same peak 86. As is visible in the depicted embodiment of FIG. 13A the stalk 16, first peak segment 82, peak 86, second peak segment 84 and the plate 30 are all integrally formed as parts of the hanger 10. Further as depicted, the length of the first peak segment 82 and the second peak segment 84 are unequal, with the former being longer than the latter. The plate 30 is a generally flat planar plate having a maximum width W1 which is at least 1.2 times the dimension of its maximum height H1. The plate 30 depends from a part of the stalk 16 and is a symmetrical about the center line "CL" of the stalk 16. The plate 30 also has a thickness "T1", and as illustrated on the figure, has top edges 31 which are generally straight and are angled downwardly with respect to the stem 16. The plate 30 includes is essentially flat and planar, and excludes any perforations passing therethrough as well as excluding any outwardly extending from either the front face 37 or the rear face 37' of the plate 30. The top edges 31 continue to the region of the side vertices 32 of the plate 30 which are rounded. The plate 30 is also generally symmetrical about a line which would extend between the two side vertices 32 of the plate 30. While not specifically disclosed in the figures, it is to be understood that the hook end 20 is flexible and in the figures shown are in a folded configuration. However, the elements of the hook end may be readily unfolded by a consumer so to adapt the hanger 10 to be suspended upon a part of a sanitary appliance. FIG. 13C illustrates a preferred embodiment wherein the plate 30 is entirely embedded within the body 50 of the lavatory treatment composition and is depicted by the phantom line. As is illustrated in the figures, the respective areas of the plate 30A and the area AB of the body 50 at the transverse plane coincident with a face of the plate 30A, further illustrating a preferred ratio of these two surface areas. In the perspective view of FIG. 13D, there is illustrated the relationship of the placement of the plate 30 within the body 50. More specifically the plane of the plate 30 is between the mid-plane MP and the front face 53 of the body 50. Further it is to be understood that dimension of the standoff element 80 is such that when the device 1 is mounted in a lavatory appliance, the standoff element 80 is of a sufficiently large dimension such that the body 50 of the lavatory treatment composition is offset, or spaced away from any physical contact with the lavatory appliance, e.g., a toilet bowl, when the lavatory treatment device 1 is mounted thereon.

Figures 14A, 14B:
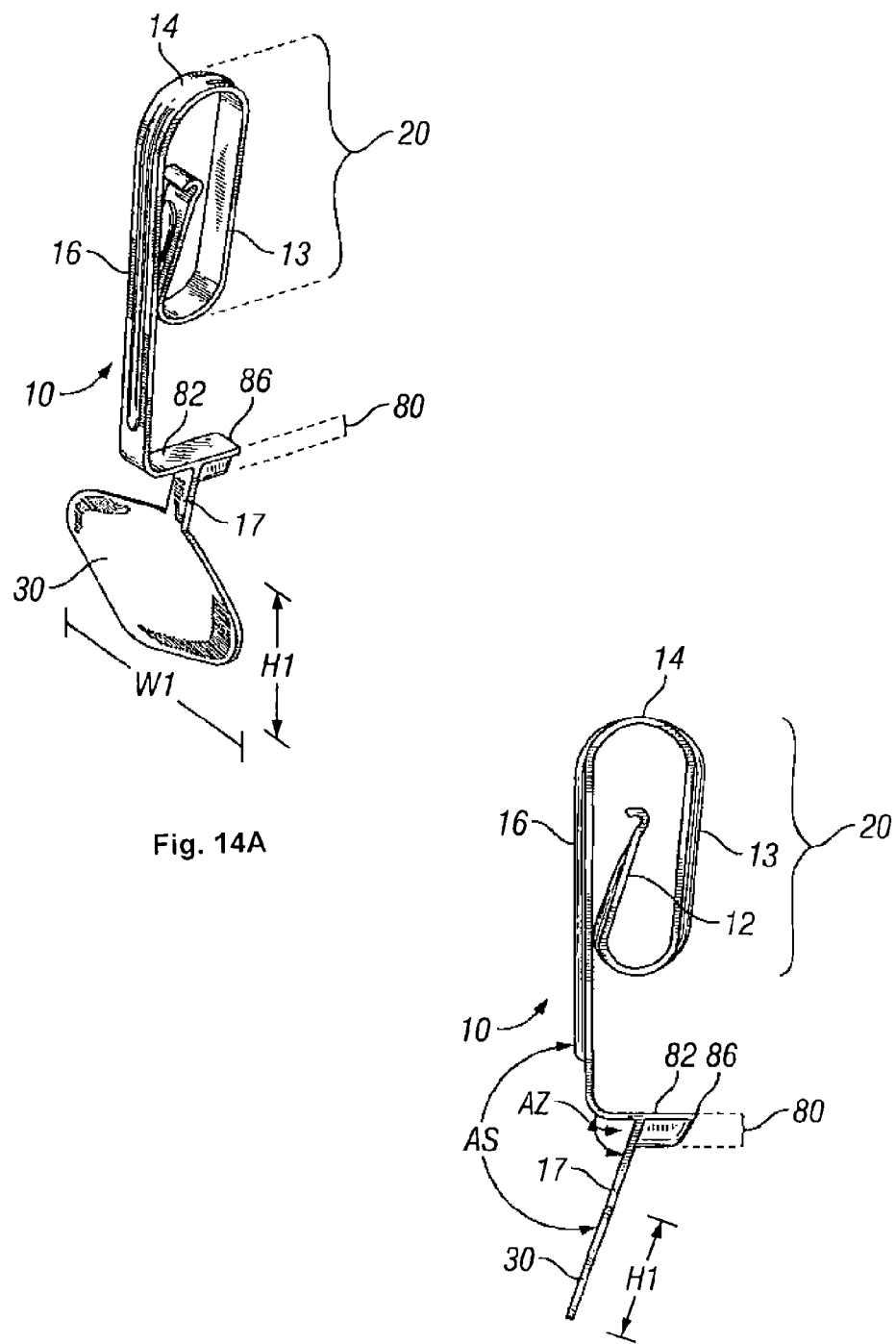
Figure 14C:
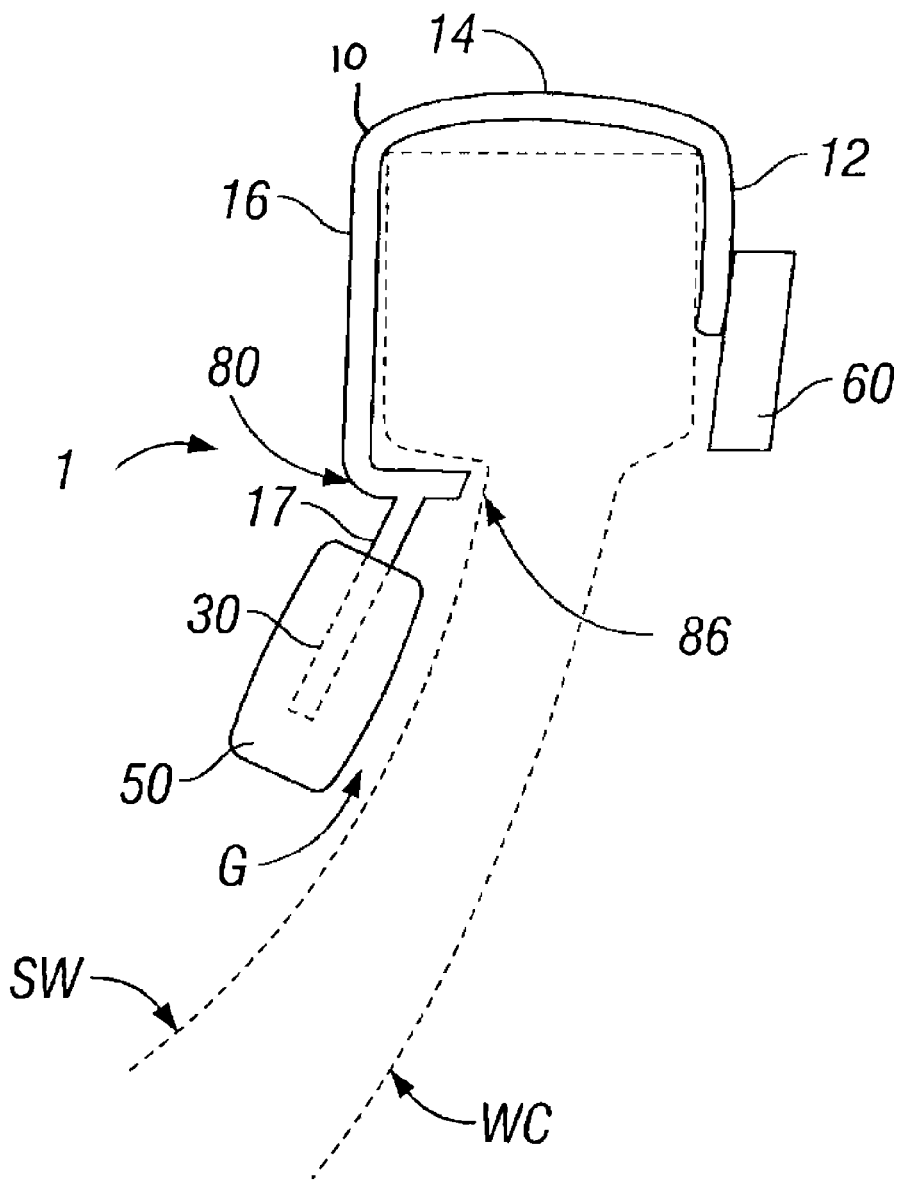

FIGS. 14A and 14B depicts a still further embodiment of a hanger 10 according to the invention which comprises a further embodiment of a peak section 80. Again, for sake of convenient reference, the body 50 of the lavatory treatment composition affixed to a part of the hanger has been omitted, but is necessarily present as described with reference to FIG. 1, as well as depicted in FIG. 14C. As is shown, the hanger includes a hook end 20 which is comprised of the end member 12, flexibly connected to an intermediate element 13, which is in turn flexibly connected to a top element 14, which in turn is flexibly connected to a part of the stalk 16. The opposite end of the stalk terminates in a generally oblate (or "diamond") shaped plate 30 having a width dimension (W1), a height dimension (H1). Whereas the hanger is depicted in a folded or otherwise coiled configuration, it is to be understood that the hook end can be extended by a user of the hanger and the lavatory treatment device to reconfigure said hook end 20 to form a hook end which can be used to suspend the hanger and the lavatory treatment device upon a part of a sanitary device particularly a toilet bowl rim. The embodiments according to FIGS. 14A and 14B also illustrate that, according to preferred embodiments, the plate 30 is substantially planar and as is shown in the figures and is of generally uniform thickness. The embodiment of the hook end 20 as depicted in the figures is preferred in that the hook end 20 is particularly well coiled when in its folded configuration, but when uncoiled or in its unfolded configuration, provides a significant degree of tension which is useful in retaining the respective position of the lavatory treatment device when installed upon a sanitary appliance, particularly when the hook is affixed on a part of a toilet bowl rim. Furthermore, as is visible the stalk 16 extends downwardly and rearwardly such that it bends in the direction of the hook end 20 and defines a first peak segment 82 which extends rearwardly from the stalk 16 to a peak 86; said first peak segment 82 which terminates at a peak 86 also simultaneously also defines a standoff. As has been discussed previously the dimensions of the standoff 80 are sufficiently large such that, preferably, the body of the lavatory treatment composition is spaced away from any direct physical contact with the lavatory appliance, e.g., a sidewall SW as disclosed on FIG. 14C. Depending downwardly from the first peak segment 82 is a bent neck 17 from which depends the plate 30. As depicted, the bent neck 17 forms an angle "AZ" with respect to the stalk 16 and also, forms a second angle "AS" between the face of the plate 30 and the stalk 16.

Desirably, in all embodiments of the invention (and not limited to the embodiment of FIGS. 14A and 14B) wherein the stalk 16 and the plate 30 are angled with respect to one another, as represented by angle AS, angle AS is between 90°-180°, but preferably is between 100° and 170°, and most preferably is between 100° and 145°. Such an angular relationship between the stalk 16 and the plate 30 are relevant to the invention wherein the hanger includes or excludes a standoff section 80. Similarly in all embodiments of the invention wherein the stalk 16 and the bent neck 17 are angled with respect to one another, as represented by angle AS, angle AS is between 0°-90°, but preferably is between 10° and 80°, and most preferably is between 15° and 55°. Such an angular positioning of the plate 30 which ultimately supports the body of the lavatory treatment composition may be advantageous. This positioning rearward of the major part of the stalk 16 is beneficial as ultimately, it acts to also thereby position the body 50 enrobing the plate 30 such that when the hanger 10 is mounted upon a toilet bowl, the body 50 of the lavatory treatment composition may be positioned in the proximity to the interior sloping side wall of a toilet bowl but spaced apart therefrom. Such positioning is advantageous in that it ensures that while the body 50 remains in the flow path of the flush water throughout the useful service life of the lavatory treatment device, such minimizes the likelihood of physical contact of the body 50 and the interior sidewall of a toilet bowl. This relationship is better understood with reference to FIG. 14C, illustrating the hanger 10 of the lavatory treatment device 1 mounted on the rim "R" of a toilet bowl "WC". A hook end 20 comprising an end element 12, and a top element 14 are configured to be suspended upon the rim of a toilet bowl "WC". The hanger 10 includes a stalk 16 which extends downwardly and includes an integrally formed standoff section 80 comprising parts of the stalk 16 adjacent to the peak point 86, which stalk 16 continues to extend downwardly and terminates via a bent neck section 17 at plate 30 which is encased in a body 50 of the lavatory treatment composition. As is seen from the figure, the dimensions of the hanger 10 are such that when it is installed in a toilet bowl, the peak point 86 contacts a part of the inner sidewall "SW" of the toilet bowl and lifts the body 50 away from the inner sidewall SW thus isolating it from physical contact with said inner sidewall SW defining an intermediate gap "G". In this manner, flush water released from the rim downwardly into the toilet bowl WC contacts the body 50 to form a lavatory treatment liquid which is used to treat the toilet bowl. Part of the flush water also flows in the gap G wherein it flushes the rear face of the body 50 as well. Subsequent to the flush cycle, the body 50 rests out of contact with the sidewall SW and above the remaining water present in the toilet bowl WC thus providing an opportunity for the body to dry between flushes. The figure further illustrates the position of an air treatment dispenser 60. The air treatment dispenser 60 is a body or a container which includes an evaporable material, e.g, a fragrance, perfume, insecticide, air sanitization composition, or the like and is mounted via the hanger 10 on the exterior of the toilet bowl WC so to supply an air treatment benefit which is directed to the exterior ambient environment of the toilet bowl WC. Such may be beneficial to provide an air treatment benefit when the interior of the toilet bowl is covered between uses, such as by a toilet seat and/or toilet set cover. It is to be understood that while not depicted, that the air treatment dispenser 60 may be mounted via the hanger 10 such that it is directed towards the interior of the toilet bowl WC so to supply an air treatment benefit which is directed to the interior ambient environment of the toilet bowl WC. For instance, the air treatment dispenser 60, 70 may be mounted on a further part of the hanger 10 such as upon the stalk 16 or bent neck 17 using suitable means. Such a configuration may be beneficial in order to provide an air treatment benefit to the interior of the toilet bowl especially when it is covered between uses, such as by a toilet seat and/or toilet set cover. In any case, the provision of an air treatment dispenser 60 as illustrated and/or as described immediately above may be omitted from any embodiment of the hanger 10, particularly if no air treatment benefit is required or desired, or wherein the composition of the body 50 contains a fragrance or other constituent which may provide an air treatment benefit.

While a specific embodiment of a hanger 10 is discussed and depicted in FIGS. 14A, 14B and 14C, such is to be understood by way of illustration and not by way of limitation and other hangers according to the invention, particularly the preferred embodiments of which are otherwise disclosed or depicted in this patent specification may be mounted upon a part of a lavatory appliance and used in a similar manner as disclosed on FIG. 14C, although not specifically depicted.

It is to be further understood that any embodiment of a lavatory treatment device may additionally include an air treatment dispenser 60, as disclosed with reference to FIG. 14C. Such an air treatment dispenser may take any suitable configuration, and may contain any evaporable or volatile material which may provide any aesthetic or technical benefit to the ambient environs of the lavatory treatment device.

Figure 15A:
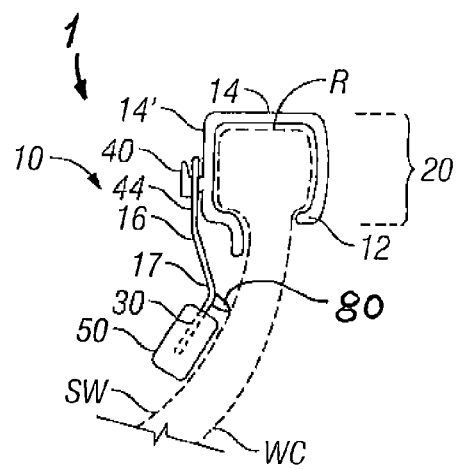
Figure 15B:
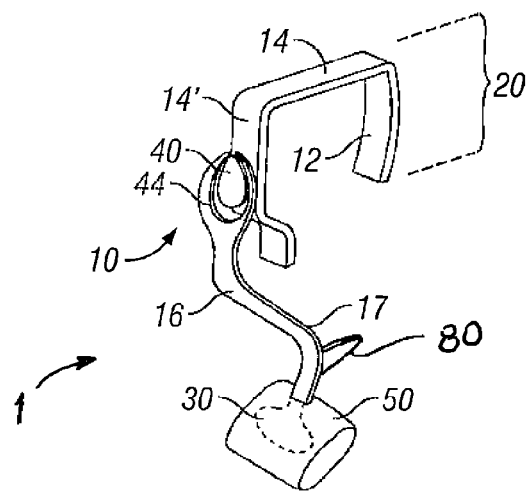

FIGS. 15A and 15B depict two views of an embodiment of a two-part lavatory treatment device 10 of the invention. FIG. 15A depicts a perspective view of a hook end 20 comprising a first element 12, a top element 14 and a front element 14' having extending from a part thereof a hanger peg 40. The hook end 20 is configured to be suspended upon the rim of a toilet bowl "WC" and may be used a single time but desirably is used several times by a consumer. The second part of the lavatory treatment device of the invention 10 includes a stalk 16 having at a proximal end an eyelet or loop 44 which is sufficiently sized so that the stalk 16 may be removably affixed to and suspended from the hanger peg 40. The stalk 16 extends downwardly from the proximal end to the distal end and includes a slanting neck 17, which terminates in plate 30 which is encased in a body 50 of a lavatory treatment composition. Intermediate the eyelet or loop 44 and the body 50 there is also present a standoff element 80 which projects rearwardly from the stalk 16 and is of sufficient dimension (e.g., length) such that in use, as depicted on FIG. 15A, the body 50 is adjacent to, but spaced away from the sidewall "SW". This second part may be installed by a user, and when the body 50 is consumed, this second part may be removed by the consumer and replaced with a further second part with a new body 50 of a lavatory treatment composition and utilized. As is more clearly depicted on FIG. 15B, the hook end 20 is mounted upon a part of a rim "R" of a toilet bowl "WC". The second part is suspended by eyelet 44 such that the body 50 is positioned adjacent to the inner sidewall "SW" of the toilet bowl WC. In this manner, flush water released from the rim downwardly into the toilet bowl WC contacts the body 50 to form a lavatory treatment liquid which is used to treat the toilet bowl.

While a cooperating hanger peg 40 and eyelet 44 exemplified one embodiment of a useful fastener means which may be used to assemble a lavatory treatment device 10, it is contemplated that any other effective means, particularly mechanical means and/or chemical means may be used as well and is considered to be within the scope of the invention, although not specifically depicted in the figures.

Figure 16A:
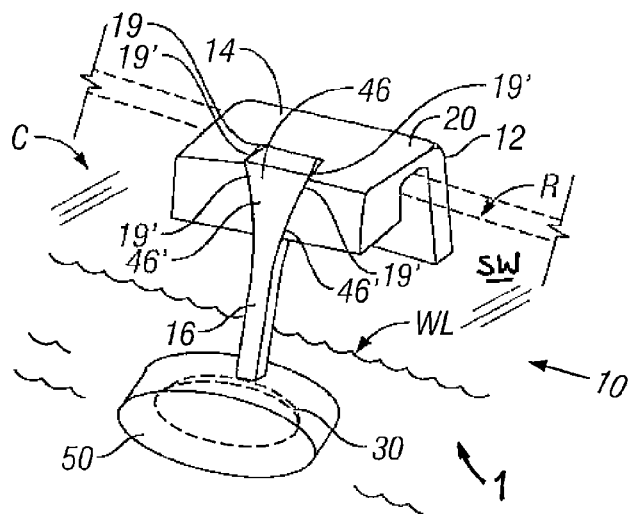
Figure 16B:
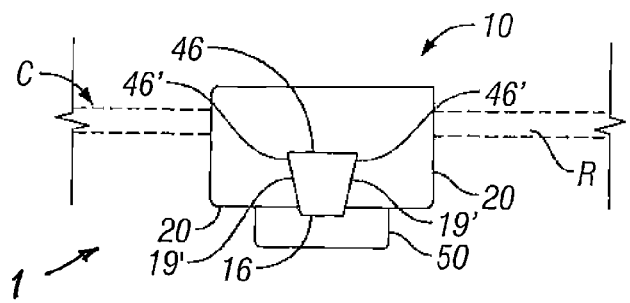

FIGS. 16A and 16B depict two views of an embodiment of a two-part lavatory treatment device 1 of the invention configured for use as an ITC device. The perspective view of FIG. 16A exemplifies a two-part lavatory dispensing device 10 comprising a first part, a rigid hook end 20 adapted to be suspended upon the rim "R" of a toilet cistern "C", and a second part, a stalk 16 having a sloped, tenon-shaped proximal end 46 inserted in a suitably shaped mortise 19 present in the hook end 20, and at its distal end a plate 30 encased by a body 50. The stalk 16 is of sufficient length that between flushes of the toilet to which it is attached, the block 50 is submerged beneath the water line "WL" so that the water contacts the block 50 to form a treatment composition within the cistern C. The top view of the lavatory treatment device 1 provided in FIG. 16B more clearly illustrates that the mortise 19 includes two sloped mortise sidewalls 19' which abut correspondingly tenon-shaped sidewalls 46' of the proximal end 46 of the stalk 16. Further, as is more apparent from FIG. 16A, the tenon-shaped sidewalls 46' of the proximal end 46 of the stalk 16 are seen to taper inwardly toward one another as well, as well as the two sloped mortise sidewalls 19' which are configured to correspondingly conform. It is to be appreciate from these figures that the configuration of the device 1 is such that the body 50 of the lavatory treatment composition is spaced away from the sidewall "SW" of the cistern.

The foregoing embodiments of the lavatory treatment device discussed with reference to the prior figures depict versions of the said device which may be called "cageless" in that the body of the lavatory treatment composition are not further enclosed in a surrounding, or partially surrounding water insoluble enclosure or housing.

Figure 17A:
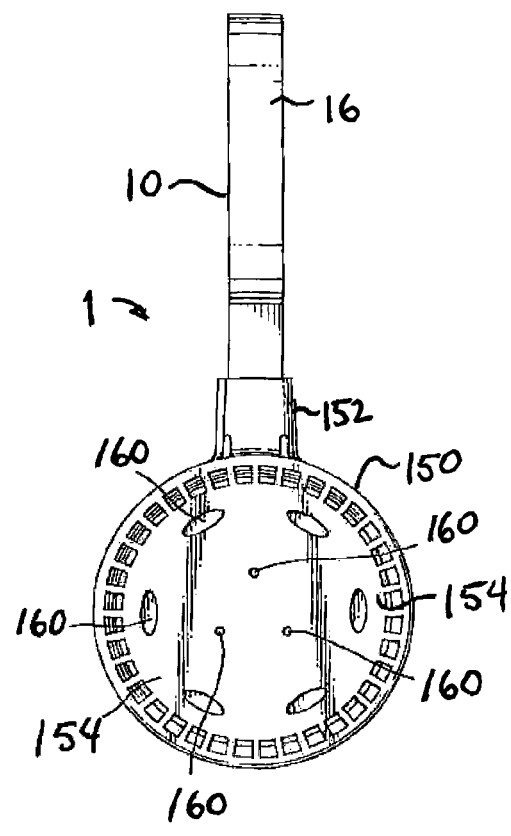
Figure 17B:
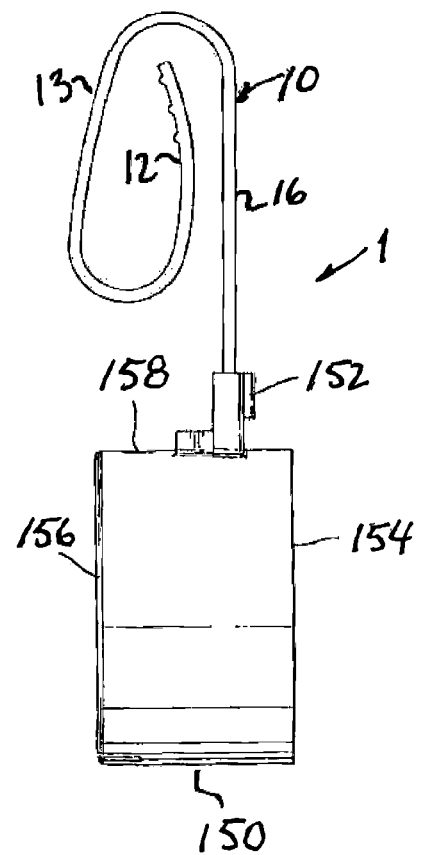

In any of the foregoing embodiments of the lavatory treatment device discussed herein, the body of the lavatory treatment composition may be partially, of wholly covered or encased in a water dispersible, water miscible or water soluble film, which may be directly applied to the body of the lavatory treatment composition, or which may be first formed into a sachet or pouch or water-soluble package into which the body of the lavatory treatment composition may be inserted into a film forming composition of a water dispersible, water miscible or water soluble material which is subsequently allowed to harden or dry to provide a barrier layer upon part or all of the surfaces of the body of the lavatory treatment composition. Such an insertion may be performed by dipping or spraying. Nonlimiting examples of useful film forming water soluble or water miscible materials include water soluble or water dispersible polymeric films (e.g. polyvinyl alcohol, or water soluble copolymer thereof, e.g, MonoSol PT 7, MonoSol M8630 ex. Chris-Craft Industrial Products; the K-series of water soluble films ex. Aicello FIGS. 17A and 17B respectively depict in a front view and a side view an embodiment of a lavatory treatment device 1 of the invention, which includes a "cage" 150 formed of a water insoluble material which encloses or surrounds a body of the lavatory treatment composition (not visible in these figures). The cage 150 depends from a part of the hanger 10 by a connecting clip 152 which may be detachable or may be permanently affixed. The cage 150 includes a front face wall 156, and a parallel, spaced apart rear face wall 154 which are interconnected by a circular sidewall 158, all of which elements define an interior cavity within the cage 150. While not visible in the drawing, a body of the lavatory treatment composition is located within this interior cavity. The front face wall 154 includes a plurality of perforations 160 which pass through the front face wall 154 and allow for the entry and egress of water into the interior cavity within the cage 150 where in comes into contact with the lavatory treatment composition. The perforations 160 also allow for the egress of formed lavatory treatment liquid out from the cage 150. In use, the lavatory treatment device 1 depicted is mounted on the rim of, or other part of, a sanitary appliance by unfolding the hook end element 12 and the second hook element 13 to extend them outwardly such that they can be suspended from the rim of a toilet bowl, or other part of a lavatory appliance, e.g., the rim of a cistern, whereby the cage 150 is positioned in water or in the path of water within the lavatory appliance.

Figure 18A:
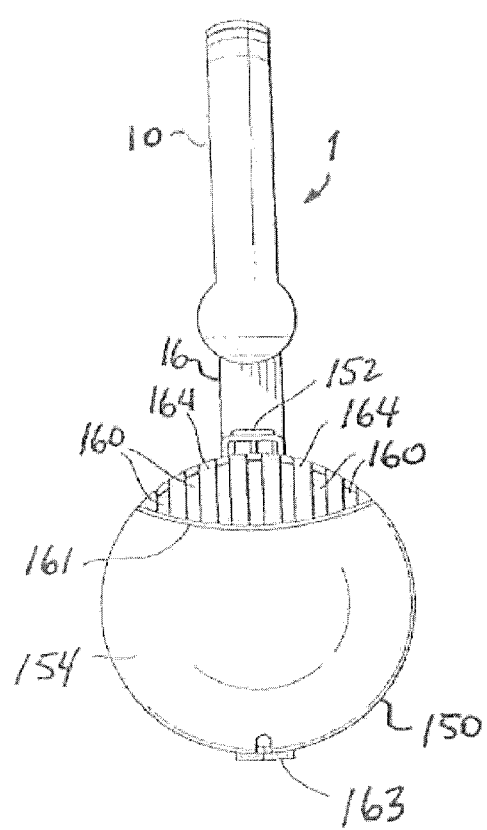
Figure 18B:
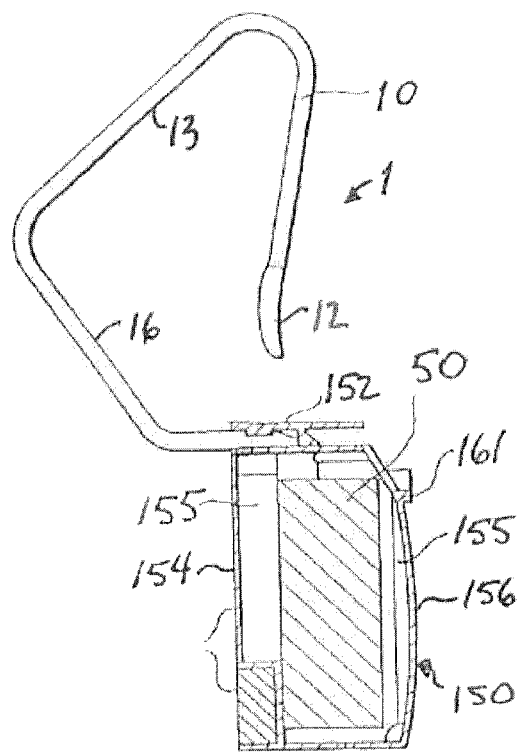

FIGS. 18A and 18B respectively depict in a front view and a cross-sectional, side view a further embodiment of a lavatory treatment device 1 of the invention, which includes a "cage" 150 formed of a water insoluble material which encloses or surrounds a body 50 of the lavatory treatment composition. In this embodiment the front face wall 156 includes a louver array 161 comprising a series of regularly spaced apart perforations 160 which is in the proximity of the connecting clip. Also provided at the opposite end of the front face wall 156 is a drain passage 163. When the lavatory treatment device 1 is mounted in the interior of a lavatory appliance, preferably the cage 150 is suspended so that the front face wall 156 is positioned in water, or in the path of water such that water is permitted to enter via the perforations 160 separated by intermediate barriers 164 of the louver array 161 and come into contact with the body 150 of the lavatory treatment composition. Thereafter, liquid treatment composition formed within the cavity 155 exits via the drain passage 163 into the lavatory appliance, and may provide a treatment benefit thereto.

In the embodiments of FIGS. 17A, 17B, 18A and 18B the provision of the cage 150 provides for a physical barrier between the body 50 of the lavatory treatment composition and any surface of the lavatory appliance, ensuring that the body 50 is isolated and spaced apart from such surface in which the cage 150 is in close proximity.

A further aspect of the invention is a method for the manufacture of lavatory treatment devices according to the present invention.

Generally, the lavatory treatment compositions may be produced by simple mixing of the constituent materials, in measured amounts, after which the formed mixture is retained in a quiescent state until a self-supporting gel, preferably a ringing gel, is formed.

A preferred method for producing the lavatory treatment compositions is as follows. To a container (e.g., an open mouthed laboratory beaker) is provided the adhesion promoter constituent based on a fatty alcohol polyglycol ether. The container is heated from room temperature (approx. 20° C.), using a combination laboratory hotplate and magnetic stirrer apparatus. At approx. 45° C. a magnetic stirring bar is introduced an stirring initiated, and continue until the adhesion promoter constituent reaches approx. 80-90° C. to ensure the full melting of the adhesion promoter constituent. Thereafter under stirring conditions are added the detersive surfactant constituent, the organic solvent constituent, and where present, the co-adhesion promoter constituent and further optional constituents except for any fragrance and colorant constituents, and optionally a part of the organic solvent constituent. The stirring is maintained until the contents of the container are homogenous, after which the heat source is deactivated or removed, and under continued stirring the contents of the container are allowed to cool. When the contents of the container reach approximately 55° C.-65° C., the fragrance and colorant constituents, and optionally a part of the organic solvent constituent are added and mixing of the contents of the beaker is continued. Next, a measured amount of water, preferably distilled or deionized water, heated to approx. 80° C. is provided in a second, larger container. Stirring is ceased, and the homogenous mixture of the first container is poured into the water of the second container and optionally mixed using a manual stirrer rod, or by a mechanical mixing means. The resultant mixture may be allowed to rest in a quiescent state at room temperature until a self-supporting gel is formed. It is observed that when the resultant mixture is provided, e.g. poured, into small form, cavity, mold or container (e.g., having a volume of less than about 100 cc, the spontaneous formation of the self-supporting gel, preferably a ringing gel, occurs at a much faster rate then were the resultant mixture is allowed to rest at room temperature in a larger form, cavity, mold or container. The resultant gel may be ejected from the form, cavity, mold or container in which it had formed, and used as a lavatory treatment composition. Alternately the resultant gel may be heated, e.g, in a microwave, until it returns to a fluid form after which it can be poured again into a form, cavity, mold or container, or other process equipment, such as a nozzle or syringe from which the lavatory treatment composition may be dispensed.

In a preferred embodiment of the foregoing process, a measured aliquot of the mixture formed from the materials described with reference to the first container are mixed with a measured aliquot of water directly within the a part of the lavatory treatment device. For example, in a "cage" type of the lavatory treatment device, the lavatory treatment composition is formed, in situ, within the cavity of the cage of the said device. Alternately where the lavatory treatment device is a "cageless" device, the measured aliquot of the mixture formed from the materials described with reference to the first container are mixed with a measured aliquot of water may be mixed, in situ, within a form, cavity, mold or container which also contains a further part of the lavatory treatment device, e.g. a plate 30 of a hanger 10, and as the gel forms, the further part is encased or enrobed by the formed gel (body) of lavatory treatment composition, and when sufficiently hard the formed lavatory treatment composition is removed or ejected form the form, cavity, mold or container. Still alternately where the lavatory treatment device is a "cageless" device, the measured aliquot of the mixture formed from the materials described with reference to the first container are mixed with a measured aliquot of water may be mixed, in situ, within a form, cavity, mold or container and either during the formation of the gel, or after the formation of the gel (body) of the lavatory treatment composition, a part of the hanger 10, e.g, a plate 30, or stalk 16, may be embedded within the gel (body.) In a still alternative method, where the lavatory treatment device is a "cageless" device, the measured aliquot of the mixture formed from the materials described with reference to the first container are mixed with a measured aliquot of water may be mixed, in situ, within a form, cavity, mold or container and either during the formation of the gel, or after the formation of the gel (body) of the lavatory treatment composition, a part of the hanger 10, e.g, a plate 30, or stalk 16, may be laid upon or otherwise adhered to a part of the hanger 10, without necessarily embedded any part of the hanger 10 within the gel (body) of the lavatory treatment composition.

Figure 19:
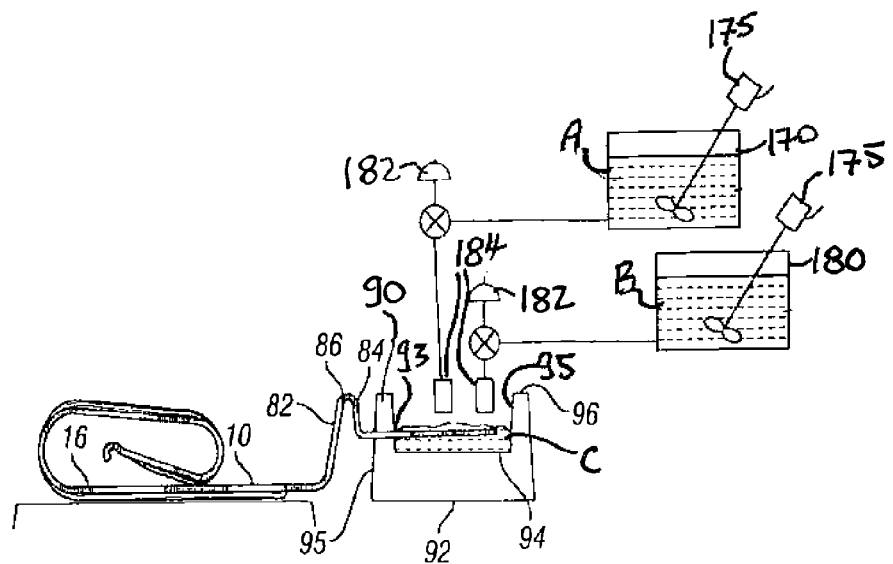
Figure 20:
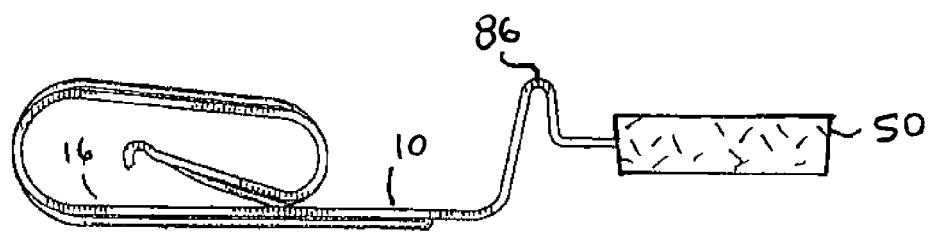

FIG. 19 illustrates a series of semi-schematic sequence of process steps illustrating a further process useful in the production of a cageless embodiment of a lavatory treatment device, as illustrated on FIG. 20. In the process, the plate 30 of a hanger 10 is supplied within the interior cavity 90 of a mold 92 wherein the plate 30 is positioned within the said cavity 90 such that it is intermediate a base or bottom of 94 of the mold, and the upper or top margin 96 of the mold 92. As is visible in this cross sectional view, the mold 92 includes a sidewall recess 93 which permits for the placement of a part of the hanger 10 to extend through a part of a sidewall 95 of this mold, such that the plate 30 may be positioned within the cavity 90. While not illustrated, a further mold element may be provided in order to seal the remaining part of the sidewall recess 93 during the filling of the cavity 90, which can be later removed in order to permit for the removal of the cast solid block 50 from the mold. The cavity 90 defines a volume within which the lavatory treatment composition may be formed, in situ. Further illustrated is a first supply tank 170 contained a homogeneously mixed premixture containing all of the nonaqueous constituents and a second supply tank 180 containing the water. The contents of the supply tanks 170, 180 contain the premixtures used to form the lavatory treatment compositions, and they are maintained at a suitable temperature (preferably at least 50° C.) and are maintained in a homogenous state by the use of suitable mechanical stirrers 175. Each of the premixtures are supplied to suitable controllable metering valves 182 which supply measured aliquots of each of the premixtures via a nozzle 184 directly to the mold 90. In operation the aliquots of the first premixture first comes into contact with the aliquot of the second premixture after each exits valve 180 and enters the mold 90, where they mix and form a gel (body) of the lavatory treatment composition which encases a part of the hanger. After the gel is sufficiently hardened, the lavatory treatment article, as illustrated on FIG. 20 is removed from the mold 90 and may be placed into use, or may be packaged for later use.

Figure 21:
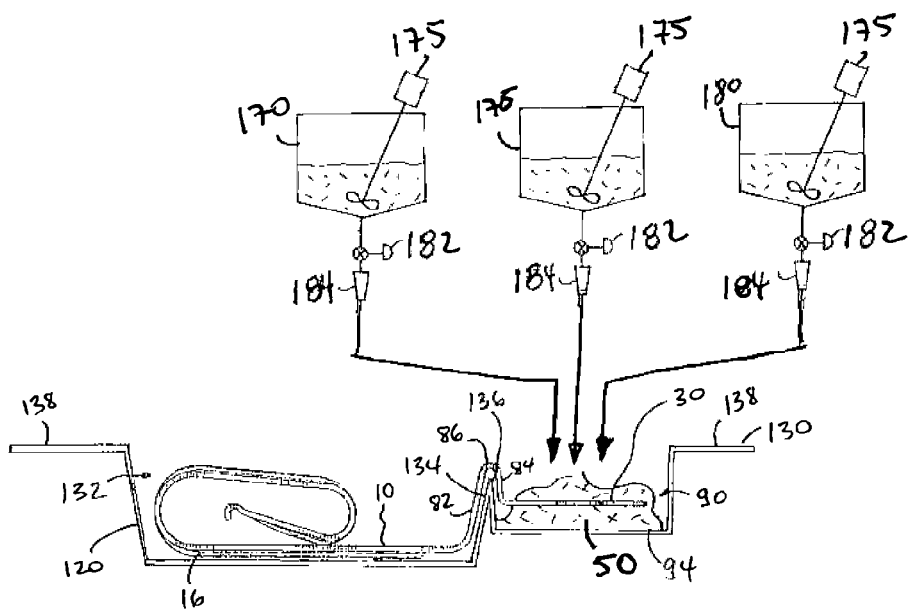

An alternative process of the manufacture of lavatory treatment devices according to the present invention utilizes the packaging in the manufacturing process. With reference to FIG. 21 thereon is depicted a series of semi-schematic sequence of process which is similar in many respects to the prior process described with reference to FIG. 19, except that the gel (body) of the lavatory treatment composition is formed, in situ, within a preformed blister 130 which includes appropriate cavities, including a cavity 90 which ultimately contains the gel (body) of the lavatory treatment composition, a hook cavity 132 within which a portion of the hanger 10 may be positioned. Intermediate these two cavities is a dividing ridge 134 which terminates at a ridge peak 136 which provides a physical division between the block cavity 90 and that the hook cavity 132.

The preformed blister 130 may be formed of any suitable material which can be formed to the ultimate desired configuration, but advantageously is any molded, thermoformed, or thermosettable synthetic plastics material, such as any thermoformed plastic sheet which is commonly encountered and used for the packaging of vendible articles wherein the blister it commonly affixed to a backing material such as a card, sheet or film which provides for further support of the vendible article contained between the interior of the blister 130 and such a backing material. Preferably, such a blister is essentially transparent as providing an attractive display. By way of nonlimiting example, useful thermoset of all synthetic plastic materials include polyolefins, polyamides, and especially polyalkylene terepthalates as well as copolymers are one or more of their of, including copolymers with further monomers or polymers not specifically disclosed herein. Typically, and as a shown on FIG. 22, the preformed blister 130 includes a generally flat, peripheral margin 138 surrounding any cavities formed within the blister, which peripheral margin 138 provides a surface against which a backing material, such as a coated paper or sheet (not shown) may be applied, and thereby sealing the preformed blister 130 and forming a package. It is contemplated that, according to the present invention, any material suitable for forming such a preformed blister 130 may be used, it only being required that the material of construction of the preformed blister 130 is not unduly deleteriously affected by the gel (body) of the lavatory treatment composition during any part of the production process, or during storage of lavatory dispensing device 1.

Further illustrated on FIG. 21 is are a plurality of supply tanks 170, 176, 180 each including a suitable mechanical stirrer 175 to ensure that the contents are retained in a homogenous condition. Each of the supply tanks 170, 176, 180 may also include a suitable conventional heating means (not shown) to maintain the contents at a desired temperature. A first supply tank 170 contains all most of the non-aqueous constituents with the possible exception of small fraction of the organic solvent constituent, a second supply tank 176 contains the fragrance material, and optionally other non-aqeuous constituents and the small fraction of the organic solvent constituent, and the third supply tank 180 contains the water. Measured amounts (aliquots) of the contents of each of the supply tanks 170, 176 and 180 are supplied via separate controllable metering valves 182 and corresponding nozzles 184 directly to the cavity 90 of the blister 130. In the cross-sectional view of FIG. 21, it can be seen and that the cavity 90 is in the process of being partially filled and that during filling, the several aliquots supplied from the supply tanks 170, 176, 180 mix with one another, and at least partially encase or fully enrobe the plate 30. Immediately following the termination of supply of the materials from supply tanks 170, 176, 180, the formation of a gel (body) of a lavatory treatment composition forms, in situ, within the cavity 90 of the blister 130. After becoming sufficiently rigid, a backing material may be applied to the preformed blister 130 thus forming a packaged lavatory treatment device 1. The lavatory treatment device 1 may later be directly removed from the blister, such as by a consumer of the device. A specific advantage of the embodiment of the process described with reference to FIG. 21 is that the ultimate product package, namely the preformed blister 130 may be used both as a mold for the gel (body) of the lavatory treatment composition 50, as well as for the subsequent storage and packaging of the cageless lavatory dispensing device 1 according to the present invention. Such is a vast simplification of the prior process described with reference to FIG. 19.

Figure 22:
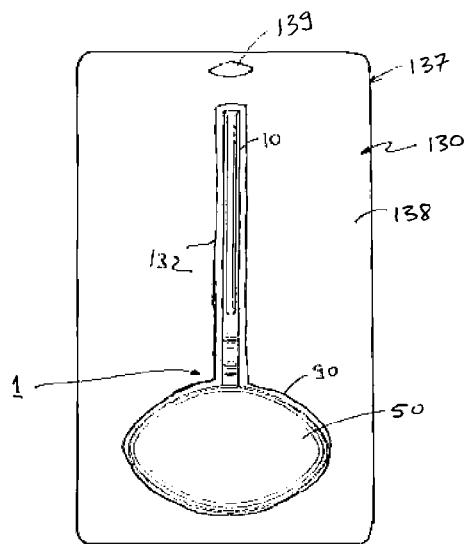

FIG. 22 depicts in a front plan view a packaged cageless lavatory dispensing device 1 of the invention which has been formed in accordance with the process described with reference to FIG. 21. As is visible thereon, the blister 130 is affixed to, such as by lamination to a backing material 137 upon the flat, peripheral margin 138 of the blister 130. Also depicted is a hole or eyelet 139 which although optional, is advantageously provided in order to conveniently hang the packaged lavatory treatment device one from a peg or hook.

A further aspect of the present invention is a vendible article comprising the lavatory treatment device described herein. Nonlimiting examples of such vendible articles are described in the foregoing specification, and preferred embodiments of vendible articles are disclosed with reference to one or more of the drawing figures, particularly the embodiments discussed herein, e.g, FIGS. 6B, 10B, 13C, 13D, 15A, 15B, 16A, 16B, 17A, 17B, 18A, 18B, 20 and 22.

EXAMPLES

Example compositions of lavatory treatment compositions according to the invention were produced, and are identified on Table 1. The compositions disclosed on Table 1 demonstrate compositions according to the invention, including certain preferred embodiments of lavatory treatment compositions of the invention. In these compositions, the constituents were used "as supplied" from their respective suppliers. The constituents constituted may have constitute less than 100% wt. "actives", or may have been supplied as constituting 100% wt. "active" of the named compound, as indicated in the following Tables 1 and Table 2. The identified amounts of each constituent on Table 1 are in "% wt." based on the total weight of a composition of which it forms a part. To each of the compositions, deionized water was added in "quantum sufficient" ("q.s.") in order to provide to 100% wt. of each lavatory treatment composition.

The lavatory treatment compositions disclosed as E1-E12 were formed generally in accordance with the following steps:

To a laboratory beaker resting upon a variable temperature controllable hotplate, which laboratory beaker was further equipped with a electrically driven stirrer was provided measured amounts of the constituents of the "Part A" premixture (e.g. Genapol® O 200, the indicated detersive surfactant, and a portion of the organic solvent constituent), and the temperature of the contents of the beaker was raised to and regulated to 80° C.-85° C., and stirring continued under these conditions until a homogenous mixture was formed. Stirring took approximately 10-20 minutes, after which, the temperature of this homogenous, first pre-mixture was allowed to reduced to approximately to 60° C.-65° C.

While the first pre-mixture was being formed, into a separate lavatory beaker resting upon a variable temperature controllable hotplate and equipped with a further electrically driven stirrer were provided measured amounts of the "Part B" constituents (a portion of the organic solvent constituent, and where present, fragrance and/or coloring agent) were supplied and stirring was initiated while the temperature of the contents of this further beaker was maintained at a suitable temperature, advantageously between about 10-60° C. Stirring of the contents of the second laboratory beaker continued until homogenous which formed the second pre-mixture. Thereafter, the second beaker was removed, and its contents were added, under stirring conditions at a temperature of between about 60° C.-65° C. to form a resultant homogenous mixture. Stirring continued for approximately 5-15 minutes. Thereafter, the stirrer was removed, and to the laboratory beaker was added a measured aliquot of the deionized water ("Part C") which is approximately room temperature and a manual stirring rod or paddle was used. It was observed that the onset of gelling within this laboratory beaker was nearly instantaneous, and the formation of a firm gel had begun in as little as 5-10 seconds after the introduction of the water. Subsequently, the manual stirring rod or paddle was removed, and set aside. The contents of the laboratory beaker was allowed to rest, overnight (approx. 12 hours) at room temperature, on a laboratory tabletop, in order to allow for the gel to fully set.

The lavatory treatment compositions according to E13-E25 of Table 1 were produced in accordance with the following general protocol. The first premix identified as Part A of Table 1 was formed by adding to a clean container (e.g., an open mouthed laboratory beaker) the adhesion promoter constituent based on a fatty alcohol polyglycol ether. The container was positioned in a combination laboratory hotplate and magnetic stirrer apparatus. The container was next heated from room temperature (approx. 20° C.), and at approx. 45° C. a magnetic stirring bar was introduced and stirring initiated, and continued until the adhesion promoter constituent reached approx. 80-90° C. to ensure the full melting of the adhesion promoter constituent had occurred. Thereafter under stirring conditions were added the remaining constituents of Part A, and stirring an heating was maintained until the contents of the container was homogenous, after which the heat source was deactivated or removed, and under continued stirring the contents of the container were allowed to cool, to 45° C.-65° C. During this time the second premix identified as Part B of Table 1 was formed in a similar manner, by mixing the constituents in a clean container, under stirring and under heating to a more moderate temperature of to approximately 55° C.-65° C., thus providing a homogenous mixture of the Part B constituents. Next, a measured amount of water, identified as Part C of Table 1, which was preferably distilled or deionized water, was heated to approx. 80° C. in a third container. When the water was sufficiently heated, the homogenous mixture of the first container and the second containers were combined, and optionally mixed, and thereafter this mixture was poured into the water of the third container and optionally mixed using a manual stirrer rod, or by a mechanical mixing means. The third container was briefly heated (approx. 2 minutes) at a low power setting (approx. 300 Watts) in a consumer grade microwave device, and thereafter was poured into one or more wide bore syringes, and allowed to rest in a quiescent state for at least 5 minutes in order to allow for the initiation of hardening and formation of a self-supporting gel. Subsequently the lavatory treatment composition was dispensed from the syringe using a mechanical press to extrude the gelled lavatory treatment compositions into a small dispensing container which contained between 3-9 grams of the gelled lavatory treatment compositions.

Alternately following mixing of Part A, Part B and Part C, the resultant lavatory treatment composition may be allowed to rest in a quiescent state at room temperature until a self-supporting gel was formed. It is observed that when the resultant mixture was provided, e.g. poured, into small form, cavity, mold or container (e.g., having a volume of less than about 100 cc, the spontaneous formation of the self-supporting gel, preferably a ringing gel, occurs at a much faster rate then were the resultant mixture is allowed to rest at room temperature in a larger form, cavity, mold or container. The resultant gel may be ejected from the form, cavity, mold or container in which it had formed, and used as a lavatory treatment composition. Alternately the resultant gel may be heated, e.g., in a microwave, until it returns to a fluid form after which it can be poured again into a form, cavity, mold or container, or other process equipment, such as a nozzle or syringe from which the lavatory treatment composition may be dispensed.

Exemplary lavatory treatment compositions according to the invention are disclosed on the following Table 1.

TABLE 1

| | | E1 | E2 | E3 | E4 | E5 | E6 | E7 |
|---|---|---|---|---|---|---|---|---|
| Part A | Genapol ® O 200 | 30 | 28 | 26 | 30 | 30 | 30 | 20 |
| | sodium lauryl ether sulfate, 3EO (70%) | 18 | 18 | 14 | 18 | 18 | 18 | 14 |
| | PEG 4000 | — | — | — | — | — | — | — |
| | mineral oil (light) | 0.5 | 0.5 | 0.5 | 0.5 | 0.5 | 0.5 | 1.0 |
| | glycerin | 0.5 | — | 0.5 | 0.5 | 0.5 | 0.5 | 0.5 |
| | propylene glycol | 3.0 | 3.0 | 2.0 | 5.0 | 5.0 | 5.0 | 7.0 |
| Part B | propylene glycol | 2.0 | — | 5.0 | — | 3.0 | 3.0 | — |
| | fragrance #1 | 3.0 | — | — | — | — | — | — |
| | fragrance #2 | — | 4.0 | 4.0 | — | — | — | — |
| | colorant #1 | — | 0.004125 | 0.004125 | — | — | — | — |
| | colorant #2 | — | 0.002000 | 0.002000 | — | — | — | — |
| | (propylene glycol from colorants #1, #2) | — | 0.606375 | 0.606375 | — | — | — | — |
| Part C | water (supplied to q.s.) | 43.0 | 45.8 | 47.3 | 46.0 | 43.0 | 43.0 | 57.5 |
| | TOTAL (% wt.): | 100 | 100 | 100 | 100 | 100 | 100 | 100 |
| | total % wt. propylene glycol from Part A and Part B | 5.00 | 3.60 | 7.60 | 5.00 | 8.00 | 8.00 | 7.00 |
| | ratio (% wt.) of propylene glycol:other organic solvents | 5:1 | 7.212:1 | 7.60:1 | 5:1 | 8:1 | 8:1 | 4.66:1 |
| | ratio (% wt.) of propylene glycol:mineral oil | 10:1 | 7.2:1 | 15.2:1 | 10:1 | 16:1 | 16:1 | 7:1 |
| | ratio (% wt.) of water:organic solvents | 10.75 | 13.11 | 15.79 | 7.66 | 7.16 | 7.16 | 6.76 |
| | ratio (% wt.) of water:propylene glycol and mineral oil | 12.28 | 13.11 | 18.95 | 8.36 | 7.81 | 7.81 | 7.18 |
| | ratio (% wt.) of water:propylene glycol onset of ringing gel properties (in hours) | 14.33 | 15.29 | 23.69 | 9.2 | 8.6 | 8.6 | 8.2 |
| | after initial formation of gel | 48+ | 48 | 24 | 24 | 24 | 24 | 12 to 18 |
| | lifespan (flush) testing (days) | NA | NA | 45+ | NA | NA | NA | NA |

| | | | E8 | E9 | E10 | E11 | E12 |
|---|---|---|---|---|---|---|---|
| | Part A | Genapol ® O 200 | 25 | 25 | 5 | 25 | 5 |
| | | Genapol ® U 300 | — | 5 | 25 | — | 25 |
| | | Praepagen HEQ (50%) | 5 | 5 | 5 | — | 5 |
| | | Crothix PA | — | — | — | — | 1 |
| | | mineral oil (light) | 2 | 2 | 2 | 4 | 2 |
| | | glycerin | 8 | 8 | 8 | 8 | — |
| | Part B | fragrance #1 | 4 | 4 | 4 | 4 | 4 |
| | | colorant #1 | 0.001 | 0.001 | 0.001 | 0.001 | 0.001 |
| | Part C | betaine surfactant (30%) | — | — | — | 25 | — |
| | | water (supplied to q.s.) | 55.99 | 50.99 | 50.99 | 33.99 | 49.99 |
| | | TOTAL (% wt.): | 100 | 100 | 100 | 100 | 100 |

| | | | E13 | E14 | E15 | E16 | E17 | E18 | E19 |
|---|---|---|---|---|---|---|---|---|---|
| | Part A | Genapol ® O 200 | 25 | — | 5 | 25 | 22 | 30 | 25 |
| | | Genapol ® U 300 | 5 | 25 | 25 | — | 6 | — | 5 |
| | | Praepagen HEQ (50%) | 5 | 5 | 5 | 5 | 5 | 5 | — |
| | | Sugaquat L1010 (35%) | — | — | — | — | — | — | 5 |
| | | mineral oil (light) | 2 | 2 | 2 | 2 | 1.5 | 1.5 | 2 |
| | | glycerin | 8 | 8 | 8 | 8 | 8 | 8 | 8 |
| | Part B | fragrance #1 | 4 | 4 | 4 | 4 | 4 | 4 | 4 |
| | | colorant #1 | 0.001 | 0.001 | 0.001 | 0.001 | 0.001 | 0.001 | 0.001 |

TABLE 1-continued

| | | E20 | E21 | E22 | E23 | E24 | E25 |
|---|---|---|---|---|---|---|---|
| Part C | preservative | 0.2 | 0.2 | 0.2 | 0.2 | 0.2 | 0.2 | 0.2 |
| | water (supplied to q.s.) | 50.379 | 55.799 | 50.799 | 55.799 | 53.299 | 51.299 | 55.799 |
| | TOTAL (% wt.): | 100 | 100 | 100 | 100 | 100 | 100 | 100 |

| | | E20 | E21 | E22 | E23 | E24 | E25 |
|---|---|---|---|---|---|---|---|
| Part A | Genapol ® O 200 | 25 | — | 25 | — | — | 5 |
| | Genapol ® U 300 | 5 | 25 | — | 40 | 50 | 40 |
| | Praepagen HEQ (50%) | — | — | — | 5 | 5 | 5 |
| | Sugaquat L1010 (35%) | 5 | 5 | 5 | — | — | — |
| | mineral oil (light) | 2 | 2 | 2 | 2.5 | 2.5 | 2 |
| | glycerin | 8 | 8 | 8 | 8 | 8 | 8 |
| Part B | fragrance #1 | 4 | 4 | 4 | 4 | 4 | 4 |
| | colorant #1 | 0.001 | 0.001 | 0.001 | 0.001 | 0.001 | 0.001 |
| Part C | preservative | 0.2 | 0.2 | 0.2 | 0.2 | 0.2 | 0.2 |
| | water (supplied to q.s.) | 55.799 | 60.799 | 60.799 | 40.299 | 30.299 | 35.799 |
| | TOTAL (% wt.): | 100 | 100 | 100 | 100 | 100 | 100 |

The identity of the constituents of Table 1 are disclosed on the following Table 2. As noted, unless otherwise indicated the constituents were provided as "100% wt. actives".

TABLE 2

| | |
|---|---|
| Genapol ® O 200 | oleyl alcohol polyglycol ether, 20 mols (avg) ethoxylation, (100% wt. actives) (ex. Clariant) |
| Genapol ® U 300 or Genapol ® O 300 | fatty alcohol polyglycol ether, 20 mols (avg) ethoxylation, (100% wt. actives) (ex. Clariant) |
| sodium lauryl ether sulfate, 3EO (70%) | sodium lauryl ether sulfate, 3 mols (avg) ethoxylation, (70% wt. actives) (ex. Rokita) |
| PEG 4000 | polyethylene glycol, (weight average) M.W. 4000, (100% wt. actives) |
| Praepagen HEQ (50%) | alkyl hydroxyethyl dimethyl ammonium chloride (50% wt. actives) (ex. Clariant) |
| betaine surfactant (30%) | betaine surfactant, supplied as AMPHOTENSID B4 (ex. Zschimmer & Schwartz Italians S.p.A) (30% wt. actives) |
| Sugaquat L1010 (35%) | stearyldimoniumhydroxypropyl decylglucosides chloride, chloride salt (35% wt. actives) |
| mineral oil (light) | technical grade light mineral oil (100% actives) (organic solvent) |
| glycerine | technical grade light mineral oil (100% actives) (organic solvent) |
| propylene glycol | technical grade supplied as (100% actives) (ex. DOW Chem. Co.) (organic solvent) |
| fragrance #1 | proprietary fragrance material |
| fragrance #2 | proprietary fragrance material |
| colorant #1 | pigment/dye (1 part pigment/dye dispersed in 99 parts of propylene glycol) |
| colorant #2 | pigment/dye (1 part pigment/dye dispersed in 99 parts of propylene glycol) |
| preservative | 1,3-dimethoyl-5,5-dimethyl hydantoin, (35-39% actives) supplied as Nipagard DMDMH |
| water | deionized water, supplied in 'quantum sufficient' (100% wt. actives) |

Samples of the compositions of the invention which were formed as described above formed "ringing gels" which were self-supporting, viz., and did not sag or run under their own weight.

The foregoing compositions E1-E7 demonstrate a first series of preferred embodiments of the inventive composition which include an anionic surfactant as an essential constituent, while the compositions of E8-E12 demonstrate compositions which do not include or require an anionic surfactant. Foregoing compositions E13-E25 demonstrate further preferred embodiments of lavatory treatment compositions of the invention.

Each of the compositions of Table 1 may be used as part of a lavatory treatment device as described herein.

While the invention is susceptible of various modifications and alternative forms, it is to be understood that specific embodiments thereof have been shown by way of example in the drawings which are not intended to limit the invention to the particular forms disclosed; on the contrary the intention is to cover all modifications, equivalents and alternatives falling within the scope and spirit of the invention as expressed in the appended claims.

The invention claimed is:

1. A lavatory dispensing device comprising a lavatory treatment composition which comprises:

up to 50% wt. of an adhesion promoter constituent based on a fatty alcohol polyglycol ether as may be represented by the following structural formula (I):

$$R-O-[CH_2-CH_2-O-]_nH \quad (I)$$

within which, R is an $C_{12}$-$C_{24}$ aliphatic mono- or polyalkene moiety, and n has a value of from 1 to 50;

1-25% wt. of an organic solvent constituent, which is liquid at room temperature (20° C.);

0.5-25% wt. of at least one detersive surfactant constituent which includes at least one cationic detersive surfactant of formula (a):

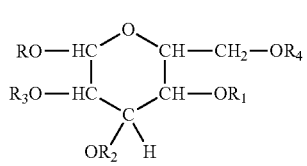

in which:

R is $C_8$-$C_{22}$ alkyl;

$R_1$, $R_2$, $R_3$ and $R_4$ are independently selected from the group consisting of: H, and the further group,

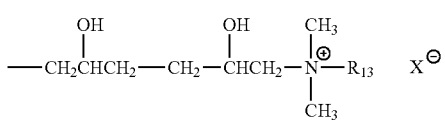

in which $R_{13}$ is $C_8$-$C_{22}$ alkyl with the proviso that $R_1$, $R_2$, $R_3$ and $R_4$ are not all H;
and X is a halogen, preferably Cl, Br or I, (b)

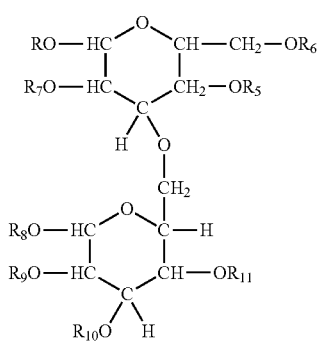

in which:
R is $C_8$-$C_{22}$ alkyl;
$R_5$, $R_6$, $R_7$, $R_8$, $R_9$, $R_{10}$ and $R_{11}$ are independently selected from the group consisting of: H, and the further group,

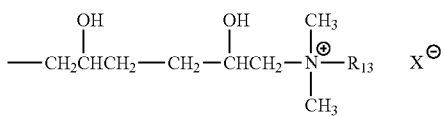

in which $R_{13}$ is $C_8$-$C_{22}$ alkyl, with the proviso that $R_5$, $R_6$, $R_7$, $R_8$, $R_9$, $R_{10}$ and $R_{11}$ are not all H;
and X is a halogen, preferably Cl, Br or I
to 100% wt. of water;
optionally a co-adhesion promoter constituent;
and, further optionally one or more further optional constituents which may impart a further aesthetic or technical benefit to the said lavatory treatment compositions.

2. A device according to claim 1, wherein in the fatty alcohol polyglycol ether of formula (I), R is a residue of a $C_{12}$-$C_{24}$ fatty alcohol having at least one unsaturated bond.

3. A device according to claim 1, wherein in the fatty alcohol polyglycol ether of formula (I), R is a residue of a $C_{12}$-$C_{24}$ fatty alcohol having is monounsaturated.

4. A device according to claim 1, wherein the said composition is a ringing gel.

5. A device according to claim 1, wherein the organic solvent constituent comprises a polyhydroxy organic solvent and at least one other organic solvent.

6. A device according to claim 5, wherein:
(a) the ratio (in % wt.) of polyhydroxy organic solvent: other solvents of the organic solvent constituent is in the range of about 4-12:1; and/or
(b) the ratio (in % wt.) of polyhydroxy organic solvent: mineral oil is in the range of about 5-20:1; and/or
(c) the ratios (in % wt.) of water:organic solvent constituent is in the range of about 5-20:1; and/or
(d) the ratios (in % wt.) of water:polyhydroxy organic solvent constituent is in the range of about 5-25:1.

7. A method for treating a lavatory appliance comprising the steps of:
mounting a lavatory dispensing device according to claim 1 to a lavatory appliance, wherein the lavatory treatment composition is in the path of flowing water, which impinges upon the lavatory treatment compositions to form a lavatory treatment liquid, and,
operating the lavatory appliance to dispense a flow of water which impinges on the lavatory treatment composition in the path of flowing water thereby forming a lavatory treatment liquid which treats the lavatory appliance.

8. A lavatory dispensing device according to claim 1, wherein the co-adhesion promoter constituent is one or more oxyalkylenated compounds.

9. A device according to claim 6, wherein:
(a) the ratio (in % wt.) of polyhydroxy organic solvent: other solvents of the organic solvent constituent is in the range of about 4.5-10:1; and/or
(b) the ratio (in % wt.) of polyhydroxy organic solvent: mineral oil is in the range of about 5-20:1; and/or
(c) the ratios (in % wt.) of water:organic solvent constituent is in the range of about 5-20:1; and/or
(d) the ratios (in % wt.) of water:polyhydroxy organic solvent constituent is in the range of about 5-25:1.

10. A device according to claim 6, wherein:
(a) the ratio (in % wt.) of polyhydroxy organic solvent: other solvents of the organic solvent constituent is in the range of about 4-12:1; and/or
(b) the ratio (in % wt.) of polyhydroxy organic solvent: mineral oil is in the range of about 7-18:1; and/or
(c) the ratios (in % wt.) of water:organic solvent constituent is in the range of about 5-20:1; and/or
(d) the ratios (in % wt.) of water:polyhydroxy organic solvent constituent is in the range of about 5-25:1.

11. A device according to claim 5, wherein:
(a) the ratio (in % wt.) of polyhydroxy organic solvent: other solvents of the organic solvent constituent is in the range of about 4-12:1; and/or
(b) the ratio (in % wt.) of polyhydroxy organic solvent: mineral oil is in the range of about 5-20:1; and/or
(c) the ratios (in % wt.) of water:organic solvent constituent is in the range of about 6-16:1; and/or
(d) the ratios (in % wt.) of water:polyhydroxy organic solvent constituent is in the range of about 5-25:1.

12. A device according to claim 5, wherein:
(a) the ratio (in % wt.) of polyhydroxy organic solvent: other solvents of the organic solvent constituent is in the range of about 4-12:1; and/or
(b) the ratio (in % wt.) of polyhydroxy organic solvent: mineral oil is in the range of about 5-20:1; and/or
(c) the ratios (in % wt.) of water:organic solvent constituent is in the range of about 5-20:1; and/or
(d) the ratios (in % wt.) of water:polyhydroxy organic solvent constituent is in the range of about 7-25:1.

* * * * *